(12) United States Patent
Lindsley et al.

(10) Patent No.: US 10,487,087 B2
(45) Date of Patent: Nov. 26, 2019

(54) POSITIVE ALLOSTERIC MODULATORS OF THE GLP-1 RECEPTOR

(71) Applicant: Vanderbilt University, Nashville, TN (US)

(72) Inventors: Craig W. Lindsley, Brentwood, TN (US); Kevin Niswender, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/067,490

(22) PCT Filed: Dec. 30, 2016

(86) PCT No.: PCT/US2016/069560
§ 371 (c)(1),
(2) Date: Oct. 1, 2018

(87) PCT Pub. No.: WO2017/117556
PCT Pub. Date: Jul. 6, 2017

(65) Prior Publication Data
US 2019/0010162 A1    Jan. 10, 2019

Related U.S. Application Data

(60) Provisional application No. 62/273,111, filed on Dec. 30, 2015.

(51) Int. Cl.
*C07D 487/04*    (2006.01)
*A61K 31/4985*   (2006.01)
*A61K 45/06*     (2006.01)

(52) U.S. Cl.
CPC ........ *C07D 487/04* (2013.01); *A61K 31/4985* (2013.01); *A61K 45/06* (2013.01); *C07B 2200/05* (2013.01)

(58) Field of Classification Search
CPC .................................................. C07D 487/04
See application file for complete search history.

(56) References Cited

U.S. PATENT DOCUMENTS

2009/0156583 A1    6/2009  Nettekoven et al.

OTHER PUBLICATIONS

Evans in "Principles of Radiopharmacology", Colombett, L.G. editor, CRC Press, pp. 11-13 and 24 (1979). (Year: 1979).*
Druck Cell Metabolism 27, Apr. 3, 2018, p. 1-17. (Year: 2018).*
Smelcerovic et al. ChemMedChem / vol. 14, Issue 5, pp. 1-21. Available online at https://onlinelibrary.wiley.com/doi/full/10.1002/cmdc.201800699 (Year: 2019).*

International Search Report and Written Opinion for Application No. PCT/US2016/069560 dated Mar. 27, 2017, 9 pages.
Ansel, "Introduction to Pharmaceutical Dosage Forms," 2nd Ed., 1976, 5 pages.
C.T.F.A. Cosmetic Ingredient Handbook, 1992, pp. 587-592.
Carruthers, "Some Modern Methods of Organic Synthesis," 3rd Edition, Cambridge University Press, Cambridge, 1987, 6 pages.
Furniss et al., "Vogel's Textbook of Practical Organic Chemistry," 5th edition (1989), Longman Scientific & Technical, Essex CM20 2JE, England, 15 pages.
Larock, "Comprehensive Organic Transformations," VCH Publishers Inc., New York, 1989, 22 pages.
Lieberman et al., "Pharmaceutical Dosage Forms: Tablets," 1981, 15 pages.
Modern Pharmaceutics, Chapters 9 and 10, Banker & Rhodes, eds., 1979, 329-427.
Remington's Pharmaceutical Sciences, 15th Ed. 1975, pp. 335-337.
Smith and March, "March's Advanced Organic Chemistry," 5th Edition, John Wiley & Sons, Inc., New York, 2001, 3 pages.
Sorrell, "Organic Chemistry," University Science Books, Sausalito, 1999, 18 pages.
Wuts, PMG, and TW Greene, "Protective Groups in Organic Synthesis," 4th ed., John Wiley & Sons, NY, 2006, 4 pages.
"McCutcheon's vol. 1, Emulsifiers & Detergents," 1994, North American Edition, pp. 236-239.
Neff et al. "Emerging role of GLP-1 receptor agonists in the treatment of obesity," Diabetes Metab Syndr Obes. 2010; 3: 263-273.
Hurtado et al., "Glucagon-Like Peptide-1 and Its Implications in Obesity," in Hot Topics in Endocrine and Endocrine-Related Diseases, Chapter 7, 2013; 165-195.
Secher et al., "The arcuate nucleus mediates GLP-1 receptor agonist liraglutide-dependent weight loss," J Clin Invest. Oct. 2014;124(10):4473-88.
Sharma et al., "GLP-1 receptor agonist liraglutide reverses long-term atypical antipsychotic treatment associated behavioral depression and metabolic abnormalities in rats," Metab Brain Dis. Apr. 2015;30(2):519-27.
McIntyre et al., "The neuroprotective effects of GLP-1: possible treatments for cognitive deficits in individuals with mood disorders," Behav Brain Res. Jan. 15, 2013;237:164-71.
Hölscher, "Central effects of GLP-1: new opportunities for treatments of neurodegenerative diseases," J Endocrinol. Mar. 7, 2014;221(1):T31-41.
Morris et al., "Discovery of (S)-2-Cyclopentyl-N-((1-isopropylpyrrolidin2-yl)-9-methyl-1-oxo-2,9-dihydro-1H-pyrrido[3,4-b]indole-4-carboxamide (VU0453379): A Novel, CNS Penetrant Glucagon-Like Peptide 1 Receptor (GLP-1R) Positive Allosteric Modulator (PAM)," J. Med. Chem., 2014, 57 (23), pp. 10192-10197.
Darsalia et al., "GLP-1R activation for the treatment of stroke: updating and future perspectives," Rev Endocr Metab Disord. Sep. 2014;15(3):233-42.

(Continued)

*Primary Examiner* — Emily A Bernhardt
(74) *Attorney, Agent, or Firm* — Michael Best & Friedrich LLP

(57) ABSTRACT

Described are positive allosteric modulators of the GLP-1 receptor, pharmaceutical compositions including the compounds, and methods of using the compounds and compositions for diabetes mellitus type 2, obesity, depression, Alzheimer's disease, Parkinson's disease, Huntington's disease, stroke, cognitive dysfunction, learning disability, and asthma in a subject.

17 Claims, 2 Drawing Sheets

(56) References Cited

OTHER PUBLICATIONS

Darsalia et al., "Glucagon-like peptide-1 receptor activation reduces ischaemic brain damage following stroke in Type 2 diabetic rats," Clin Sci (Lond). May 1, 2012;122(10):473-83.
Mattson et al., "Learning from the gut," Nature Medicine, 2003; 9(9): 1113-1115.
Morris et al., "A Duplexed High-Throughput Screen to Identify Allosteric Modulators of the Glucagon-Like Peptide 1 and Glucagon Receptors," J Biomol Screen. Jul. 2014; 19(6): 847-858.
Goebel-Stengel et al., "The importance of using the optimal plasticware and glassware in studies involving peptides," Anal Biochem. Jul. 1, 2011;414(1):38-46.

\* cited by examiner

| | GLP-1 (7-36) NH$_2$ | GLP-1 (7-36) NH$_2$ + 30μM PAM | GLP-1 (7-36) NH$_2$ + 10μM PAM | GLP-1 (7-36) NH$_2$ + 3μM PAM | GLP-1 (7-36) NH$_2$ + 1μM PAM |
|---|---|---|---|---|---|
| EC$_{50}$ | 21 nM | 9.6 nM | 12 nM | 14 nM | 20 nM |
| %E$_{MAX}$ | | 118% | 112% | 111% | 102% |
| Fold-Shift | | 2.24 | 1.72 | 1.57 | 1.05 |

POSITIVE ALLOSTERIC MODULATORS OF THE GLP-1 RECEPTOR

CROSS-REFERENCE TO RELATED APPLICATION

This patent application is the U.S. national stage entry, under 35 U.S.C. § 371, of international application number PCT/US2016/069560, filed Dec. 30, 2016, which claims the benefit of priority to U.S. Provisional Application No. 62/273,111, filed on Dec. 30, 2015, the entire contents of which are hereby incorporated by reference, and priority to which is hereby claimed.

STATEMENT OF GOVERNMENT INTEREST

This invention was made with government support under Grant number 5R01 GM106232 awarded by the National Institutes of Health; under Grant number 5P30DK020593 awarded by the National Institutes of Health; and under Grant number 1-10-BS-134 by the American Diabetes Association. The government has certain rights in the invention.

TECHNICAL FIELD

The present disclosure relates to compounds, compositions, and methods for treating glucagon-like peptide-1 receptor related diseases and/or disorders, such as type 2 diabetes, obesity, depression, Alzheimer's disease, Parkinson's disease, Huntington's disease, stroke, cognitive dysfunction, learning disability, and asthma.

BACKGROUND

The present disclosure relates to compounds, compositions, and methods for treating glucagon-like peptide-1 receptor related diseases and/or disorders, such as type 2 diabetes, obesity, depression, Alzheimer's disease, Parkinson's disease, Huntington's disease, stroke, cognitive dysfunction, learning disability, and asthma.

Type 2 diabetes is a prevalent metabolic disorder characterized by relative insulin deficiency, insulin resistance, and hyperglycemia. Pathologically, pancreatic β cells found in the Islets of Langerhans become progressively dysfunctional and unable to keep up with the demand for increased insulin secretion in the setting of insulin resistance. Ultimately β cells become highly metabolically stressed, and undergo apoptotic cell death, leading to progressively worsening dysglycemia. Concomitant with β cell dysfunction, a cell dysfunction also occurs in diabetes. In this case, the α cells overproduce glucagon, which causes the liver to overproduce glucose, leading to fasting hyperglycemia. The α cells in diabetes no longer respond to normal cues to suppress glucagon production. Obesity is frequently co-morbid with diabetes, and is an important cause of the insulin resistance and is a major risk factor for diabetes. Chronic hyperglycemia and hyperlipidemia contributes to microvascular complications such as neuropathy, retinopathy, nephropathy, and macrovascular disease, such as coronary artery disease and stroke.

Glucagon-like peptide-1 (GLP-1) is synthesized and processed in enteroendocrine L cells in the gut and is released into the local circulation upon nutrient ingestion. It has numerous salutary effects throughout the body by activating its group B G-protein coupled receptor (GPCR). GLP-1 receptors (GLP1R) are expressed in pancreatic β cells where GLP-1 action substantially amplifies insulin secretion, also known as the "incretin effect." Glucagon over-secretion is an increasingly recognized pathophysiological feature of diabetes, and GLP-1 via GLP1R suppresses glucagon release from α cells. GLP-1 does not increase insulin secretion under euglycemic conditions, nor does it suppress glucagon secretion under hypoglycemic conditions. Thus, diabetes therapeutics that capitalize on the GLP-1 axis have a low risk of hypoglycemia and a significant safety advantage.

A number of effects can be attributed to GLP-1 action in peripheral tissues other than the pancreas and in the CNS. These include effects on CNS control of peripheral glucose homeostasis, lipid metabolism, neuroprotection (Huntington's, Parkinson's, Alzheimier's, stroke), learning and memory, stress and illness responses. GLP-1 is synthesized in the CNS and functions as a neurotransmitter. GLP1R are widely distributed in the CNS where they mediate these pleotropic effects. They are also found in the mediobasal hypothalamus, where activation reduces feeding and weight gain.

Because GLP-1 has been implicated in many diseases and/or disorders, targeting the GLP-1 axis has been the subject of much investigation. Several reports have highlighted its link to a variety of diseases, such as Type 2 diabetes, obesity, depression, Alzheimer's, Parkinson's, and Huntington's disease, stroke, cognitive dysfunction, learning disability, and asthma.

SUMMARY OF THE INVENTION

In one aspect, disclosed are compounds of formula (I),

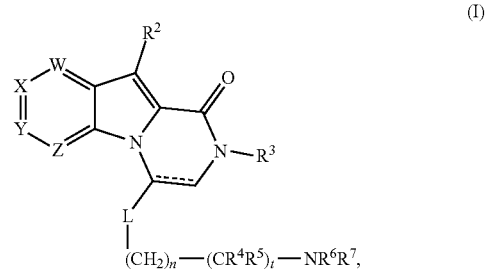

(I)

or a pharmaceutically acceptable salt thereof; wherein W is CR' or N; X is CR' or N; Y is CR' or N; Z is CR' or N; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle.; wherein said aryl, heteroaryl, cycloalkyl, and heterocycle, at each occurrence, are independently substituted or unsubstituted. In certain embodiments, $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl and haloalkyl.

Also disclosed are pharmaceutical compositions comprising the compounds, methods of making the compounds, and methods of using the compounds for treatment of glucagon-like peptide-1 receptor related diseases and/or disorders.

DETAILED DESCRIPTION

Figure 1:
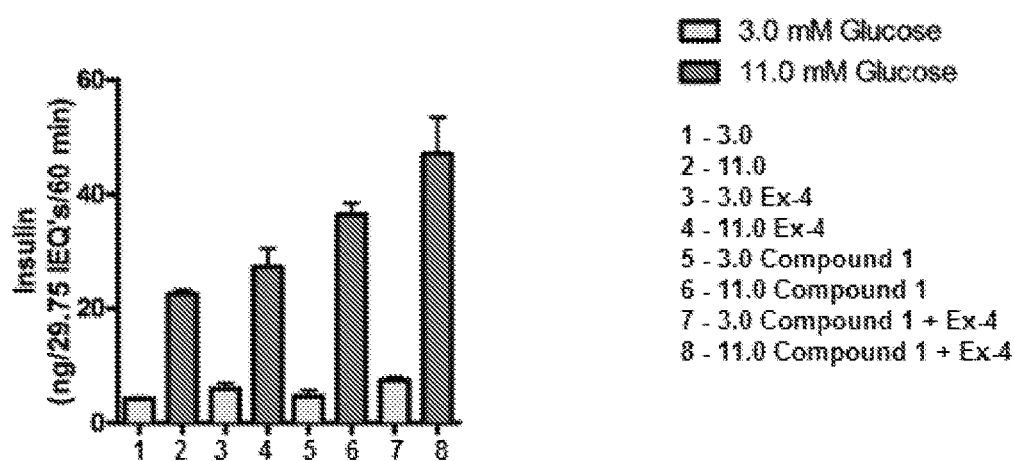
FIG. 1 shows measurement of the effect of 5 uM of Compound 1, a GLP-1 PAM, on potentiation of glucose-stimulated insulin secretion in primary human pancreatic islets under low gluocose (3 uM) and high glucose (11 uM) and in the presence or absence of 10 nM exendin-4 (orthosteric peptide agonist).
Figures 2A, 2B:
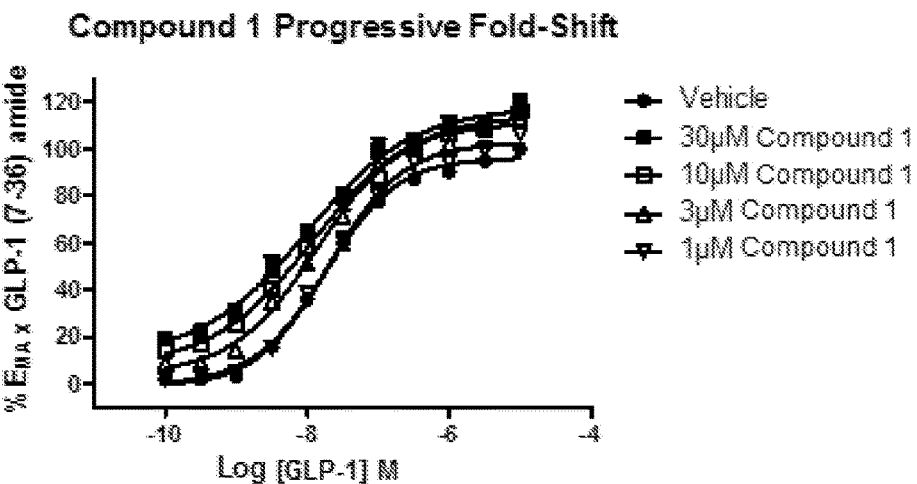
FIGS. 2A and 2B show a series of GLP-1 concentration response curves in the presence of fixed concentrations of an exemplary positive allosteric modulator (Compound 1). The series of curves demonstrate increased potentiation of GLP-1 action with increased concentration (0 μM, 3 μM, 10 μM, 30 μM) of Compound 1. Increased concentrations of Compound 1 induced a leftward shift in the GLP-1 concentration response curves for GLP-1 induced calcium flux, resulting in an accompanying decrease in GLP-1 $EC_{50}$.

Disclosed herein are positive allosteric modulators (PAMs) of GLP1R, as well as ago-PAMs. The modulators may exhibit no ligand bias, and potentiate all endogenous forms of GLP. The modulators can have formula (I). Compounds of formula (I) can be used to treat or prevent diseases and disorders associated with GLP-1 by modulating GLP1R activity to promote GLP-1 action. GLP-1 action has been implicated in a number of different diseases and disorders including, but not limited to, Type 2 diabetes, obesity, depression, Alzheimer's, Parkinson's, and Huntington's disease, stroke, cognitive dysfunction, learning disability, and asthma.

GLP-1 has a very short in vivo half-life due to the activity of dipeptidyl peptidase 4 (DPPIV), thus it has not been an attractive therapeutic. Known DDPIV inhibitors are orally bioavailable, but have modest efficacy and little effect on weight. DPPIV resistant peptide GLP-1 analogues (e.g., exenatide and liraglutide) have been developed and have proven efficacious. They do induce weight loss concomitant with improved glycemic control another major advantage given the role of weight and obesity in diabetes pathogenesis. However, side effects of injectable agents such as these substantially limit long term adherence.

GLP1R has not been successfully clinically targeted with small molecule allosteric modulator based therapeutics. Family B GPCRs have large, complex orthosteric binding sites and complex peptide agonists, making development of small molecule agonists challenging. Because of the size and complexity of the orthosteric site, allosteric modulation is a pharmacologically attractive and innovative mode of targeting GLP1R to induce receptor activation and amplify signals generated by endogenous ligands in a temporally and spatially preserved manner. Hence, positive allosteric modulation and/or allosteric agonism (ago-PAMs) of GLP1R can provide therapeutic benefits for disorders associated with GLP-1.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* 3$^{rd}$ Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 10 carbon atoms. The term "lower alkyl" or "$C_1$-$C_6$-alkyl"

means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a straight or branched, hydrocarbon chain containing at least one carbon-carbon double bond and from 1 to 10 carbon atoms.

The term "alkoxyalkyl" as used herein, refers to an alkoxy group, as defined herein, appended to the parent molecular moiety through an alkyl group, as defined herein.

The term "alkoxyfluoroalkyl" as used herein, refers to an alkoxy group, as defined herein, appended to the parent molecular moiety through a fluoroalkyl group, as defined herein.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH_2CH_2CH_2$—, and $CH_2CH_2CH_2CH_2CH_2$—.

The term "alkylamino" as used herein, means at least one alkyl group, as defined herein, is appended to the parent molecular moiety through an amino group, as defined herein.

The term "amide" as used herein, means —C(O)$NR^d$— or —$NR^dC(O)$—, wherein $R^d$ may be hydrogen, alkyl, cycloalkyl, aryl, heteroaryl, heterocycle, alkenyl, or heteroalkyl.

The term "aminoalkyl" as used herein, means at least one amino group, as defined herein, is appended to the parent molecular moiety through an alkylene group, as defined herein.

The term "amino" as used herein, means —$NR^xR^y$, wherein $R^x$ and $R^y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be —$NR^x$—, wherein $R^x$ may be hydrogen, alkyl, cycloalkyl, aryl, heteroaryl, heterocycle, alkenyl, or heteroalkyl.

The term "aryl" as used herein, refers to a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, and tetrahydroquinolinyl.

The term "cyanoalkyl" as used herein, means at least one —CN group, is appended to the parent molecular moiety through an alkylene group, as defined herein.

The term "cyanofluoroalkyl" as used herein, means at least one —CN group, is appended to the parent molecular moiety through a fluoroalkyl group, as defined herein.

The term "cycloalkoxy" as used herein, refers to a cycloalkyl group, as defined herein, appended to the parent molecular moiety through an oxygen atom.

The term "cycloalkyl" as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl.

The term "cycloalkenyl" as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "fluoroalkyl" as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "fluoroalkoxy" as used herein, means at least one fluoroalkyl group, as defined herein, is appended to the parent molecular moiety through an oxygen atom. Representative examples of fluoroalkyloxy include, but are not limited to, difluoromethoxy, trifluoromethoxy and 2,2,2-trifluoroethoxy.

The term "halogen" or "halo" as used herein, means Cl, Br, I, or F.

The term "haloalkyl" as used herein, means an alkyl group, as defined herein, in which one, two, three, four, five, six, seven or eight hydrogen atoms are replaced by a halogen.

The term "haloalkoxy" as used herein, means at least one haloalkyl group, as defined herein, is appended to the parent molecular moiety through an oxygen atom.

The term "halocycloalkyl" as used herein, means a cycloalkyl group, as defined herein, in which one or more hydrogen atoms are replaced by a halogen.

The term "heteroalkyl" as used herein, means an alkyl group, as defined herein, in which one or more of the carbon atoms has been replaced by a heteroatom selected from S, a P and N. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, benzimidazolyl, benzothiazolyl, benzoxazolyl, benzothienyl, benzofuranyl, isobenzofuranyl, furanyl, oxazolyl, isoxazolyl, purinyl, isoindolyl, quinoxalinyl, indazolyl, quinazolinyl, 1,2,4-triazinyl, 1,3,5-triazinyl, isoquinolinyl and quinolinyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "hydroxyl" or "hydroxy" as used herein, means an —OH group.

The term "hydroxyalkyl" as used herein, means at least one —OH group, is appended to the parent molecular moiety through an alkylene group, as defined herein.

The term "hydroxyfluoroalkyl" as used herein, means at least one —OH group, is appended to the parent molecular moiety through a fluoroalkyl group, as defined herein.

In some instances, the number of carbon atoms in a hydrocarbyl substituent (e.g., alkyl or cycloalkyl) is indicated by the prefix "$C_x$-$C_y$—", wherein x is the minimum and y is the maximum number of carbon atoms in the substituent. Thus, for example, "$C_1$-$C_3$-alkyl" refers to an alkyl substituent containing from 1 to 3 carbon atoms.

The term "sulfonamide" as used herein, means —S(O)$_2$NR$^d$— or —NR$^d$S(O)—, wherein R$^d$ may be hydrogen, alkyl, cycloalkyl, aryl, heteroaryl, heterocycle, alkenyl, or heteroalkyl.

The term "substituents" refers to a group "substituted" on an aryl, heteroaryl, phenyl or pyridinyl group at any atom of that group. Any atom can be substituted.

The term "substituted" refers to a group that may be further substituted with one or more non-hydrogen substituent groups Substituent groups include, but are not limited to, halogen, =O, =S, cyano, nitro, fluoroalkyl, alkoxyfluoroalkyl, fluoroalkoxy alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, atylalkyl, hydroxy, hydroxyalkyl, alkoxy, alkoxyalkyl, alkylene, aryloxy, phenoxy, benzyloxy, amino, alkylamino, acylamino, aminoalkyl, acylamino, sulfonylamino, sulfinylamino, sulfonyl, alkylsulfonyl, arylsulfonyl, aminosulfonyl, sulfinyl, —COOH, ketone, amide, carbamate, and acyl.

The term "═══" designates a single bond (——) or a double bond (══).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

In one aspect, disclosed is a compound of formula (I):

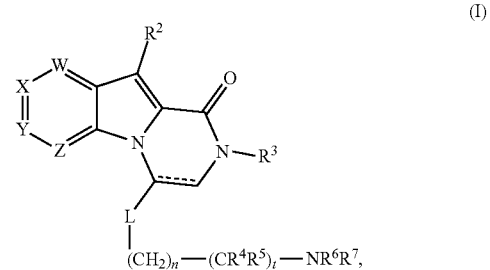

or a pharmaceutically acceptable salt thereof, wherein W is CR$^1$ or N; X is CR$^1$ or N; Y is CR$^1$ or N; Z is CR$^1$ or N; R$^1$, at each occurrence, is independently selected from the group consisting of hydrogen, alkyl, alkenyl, cycloalkyl, halogen, alkoxy, cycloalkoxy, heteroalkyl, cyano, SO$_2$R$^a$, NR$^b$R$^c$, C(O)NR$^b$R$^c$, hydroxyl, heterocycle, heteroaryl, and haloalkyl; R$^2$ is hydrogen, alkyl, alkenyl, cycloalkyl, halogen, alkoxy, cycloalkoxy, heteroalkyl, cyano, SO$_2$R$^a$, NR$^b$R$^c$, hydroxyl, heterocycle, heteroaryl or haloalkyl; R$^3$ is alkyl, cycloalkyl, heterocycle, aryl, heteroaryl, SO$_2$R$^a$, or haloalkyl; R$^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted. In certain embodiments, $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl and haloalkyl.

In certain embodiments, W is $CR^1$ or N; X is $CR^1$ or N; Y is $CR^1$ or N; Z is $CR^1$ or N; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, C(O)$NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted with 1, 2, 3, 4, 5, 6, or 7 functional groups independently selected from the group consisting of halogen, =O, =S, cyano, cyanoalkyl, cyanofluoroalkyl, nitro, fluoroalkyl, alkoxyfluoroalkyl, fluoroalkoxy, alkyl, alkenyl, alkynyl, haloalkyl, haloalkoxy, heteroalkyl, cycloalkyl, halocycloalkyl, cycloalkenyl, aryl, heteroaryl, heterocycle, cycloalkylalkyl, heteroarylalkyl, arylalkyl, hydroxy, hydroxyalkyl hydroxyfluoroalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, COOH, ketone, amide, carbamate, and acyl.

In certain embodiments, $R^1$, at each occurrence, is independently selected from the group consisting of hydrogen, $C_1$-$C_3$ alkyl, $C_2$-$C_4$ alkenyl, $C_3$-$C_6$ cycloalkyl, halogen, $C_1$-$C_3$ alkoxy, $C_3$-$C_6$ cycloalkoxy, heteroalkyl, cyano, $SO_2R^a$, $NR^bR^c$, hydroxyl, heterocycle, heteroaryl, $CFH_2$, $CF_2H$, and $CF_3$; $R^2$ is hydrogen, $C_1$-$C_3$ alkyl, $C_2$-$C_4$ alkenyl, $C_3$-$C_6$ cycloalkyl, halogen, $C_1$-$C_3$ alkoxy, $C_3$-$C_6$ cycloalkoxy, cyano, $SO_2R^a$, $NR^bR^c$, hydroxyl, heterocycle, heteroaryl, $CFH_2$, $CF_2H$, or $CF_3$; $R^3$ is $C_1$-$C_3$ alkyl, $C_3$-$C_6$ cycloalkyl, heterocycle, heteroaryl, aryl, $SO_2R^a$, $CFH_2$, $CF_2H$, or $CF_3$; L is —C(O)$NR^d$—, —$NR^d$C(O)—, —$OCH_2$—, —$CH_2O$—, —$SO_2CH_2$—, —$CH_2SO_2$—, —$CH_2CH_2$—, —$CH_2NR^d$—, or —$NR^dCH_2$—; $R^d$ is hydrogen or $C_1$-$C_3$ alkyl; $R^4$ and $R^5$ are each independently hydrogen, $C_1$-$C_3$ alkyl, or $C_1$-$C_3$ haloalkyl; and $R^6$ and $R^7$ are each independently selected from the group consisting of hydrogen, $C_1$-$C_3$ alkyl, $C_3$-$C_6$ cycloalkyl, heterocycle, heteroaryl, $CFH_2$, $CF_2H$, and $CF_3$; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, $R^1$, at each occurrence, is independently selected from the group consisting of hydrogen, $C_1$-$C_3$ alkyl, $C_2$-$C_4$ alkenyl, $C_3$-$C_6$ cycloalkyl, halogen, $C_1$-$C_3$ alkoxy, $C_3$-$C_6$ cycloalkoxy, heteroalkyl, cyano, $SO_2R^a$, $NR^bR^c$, hydroxyl, heterocycle, heteroaryl, $CFH_2$, $CF_2H$, and $CF_3$; $R^2$ is hydrogen, $C_1$-$C_3$ alkyl, $C_2$-$C_4$ alkenyl, $C_3$-$C_6$ cycloalkyl, halogen, $C_1$-$C_3$ alkoxy, $C_3$-$C_6$ cycloalkoxy, cyano, $SO_2R^a$, $NR^bR^c$, hydroxyl, heterocycle, heteroaryl, $CFH_2$, $CF_2H$, or $CF_3$; $R^3$ is $C_1$-$C_3$ alkyl, $C_3$-$C_6$ cycloalkyl, heterocycle, heteroaryl, aryl, $SO_2R^a$, $CFH_2$, $CF_2H$, or $CF_3$; L is —C(O)$NR^d$—, —$NR^d$C(O)—, —$OCH_2$—, —$CH_2O$—, —$SO_2CH_2$—, —$CH_2SO_2$—, —$CH_2CH_2$—, —$CH_2NR^d$—, or —$NR^dCH_2$—; $R^d$ is hydrogen or $C_1$-$C_3$ alkyl; $R^4$ and $R^5$ are each independently hydrogen, $C_1$-$C_3$ alkyl, or $C_1$-$C_3$ haloalkyl; and $R^6$ and $R^7$ are each independently selected from the group consisting of hydrogen, $C_1$-$C_3$ alkyl, $C_3$-$C_6$ cycloalkyl, heterocycle, heteroaryl, $CFH_2$, $CF_2H$, and $CF_3$; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted with 1, 2, 3, 4, 5, 6, or 7 functional groups independently selected from the group consisting of halogen, =O, =S, cyano, cyanoalkyl, cyanofluoroalkyl, nitro, fluoroalkyl, alkoxyfluoroalkyl, fluoroalkoxy, alkyl, alkenyl, alkyny, haloalkyl, haloalkoxy, heteroalkyl, cycloalkyl, halocycloalkyl, cycloalkenyl, aryl, heteroaryl, heterocycle, cycloalkylalkyl, heteroarylalkyl, arylalkyl, hydroxy, hydroxyalkyl, hydroxyfluoroalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

In certain embodiments, W is $CR^1$ or N; X is $CR^1$ or N; Y is $CR^1$ or N; and Z is $CR^1$ or N.

In certain embodiments, W and Y are each $CR^1$. In certain embodiments, W and Y are each $CR^1$, and X and Z are each independently N or $CR^1$.

In certain embodiments, W and Y are each $CR^1$, and X and Z are each N. In certain embodiments, X and Z are each $CR^1$, and W and Y are each N. In certain embodiments, X and Y are each $CR^1$, and W and Z are each N. In certain embodiments, W and X are each $CR^1$, and Y and Z are each N. In certain embodiments, Y and Z are each $CR^1$, and W and X are each N.

In certain embodiments, W, X and Y are each $CR^1$, and Z is N. In certain embodiments, W, X and Z are each $CR^1$, and Y is N. In certain embodiments, W, Y and Z are each $CR^1$, and X is N. In certain embodiments, X, Y and Z are each $CR^1$, and W is N.

In certain embodiments, W, X, Y and Z are each $CR^1$.

In certain embodiments, $R^c$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^a$, at each occurrence, is independently selected from the group consisting of alkyl, cycloalkyl, heterocycle, heteroaryl, aryl, heteroalkyl, and $NR^bR^c$; and $R^b$ and $R^c$, at each occurrence, are each independently selected from the group consisting of hydrogen, alkyl, cycloalkyl, heterocycle, heteroaryl, and heteroalkyl.

In certain embodiments, $R^c$, at each occurrence, is independently selected from the group consisting of hydrogen, $C_1$-$C_3$ alkyl, $C_2$-$C_4$ alkenyl, $C_3$-$C_6$ cycloalkyl, halogen, $C_1$-$C_3$ alkoxy, $C_3$-$C_6$ cycloalkoxy, cyano, heteroalkyl, $SO_2R^a$, $NR^bR^c$, hydroxyl, heterocycle, heteroaryl, and $C_1$-$C_3$ haloalkyl; $R^a$, at each occurrence, is independently selected from the group consisting of alkyl, cycloalkyl, heterocycle, heteroaryl, aryl, heteroalkyl, and $NR^bR^c$; and $R^b$ and $R^c$, at each occurrence, are each independently selected from the group consisting of hydrogen, alkyl, cycloalkyl, heterocycle, heteroaryl, and heteroalkyl.

In certain embodiments, $R^1$, at each occurrence, is independently selected from the group consisting of hydrogen, $C_1$-$C_3$ alkyl, halogen, $C_1$-$C_3$ alkoxy, cyano, $CFH_2$, $CF_2H$, and $CF_3$.

In certain embodiments, $R^1$, at each occurrence, is independently selected from the group consisting of hydrogen and halogen.

In certain embodiments, W, X, Y and Z are each $CR^1$; $R^1$, at each occurrence, is independently selected from the group consisting of hydrogen, $C_1$-$C_3$ alkyl, $C_2$-$C_4$ alkenyl, $C_3$-$C_6$ cycloalkyl, halogen, $C_1$-$C_3$ alkoxy, $C_3$-$C_6$ cycloalkoxy, heteroalkyl, cyano, $SO_2R^a$, $NR^bR^c$, hydroxyl, heterocycle, heteroaryl, and $C_1$-$C_3$ haloalkyl; $R^a$, at each occurrence, is independently selected from the group consisting of alkyl, cycloalkyl, heterocycle, heteroaryl, aryl, heteroalkyl, and $NR^bR^c$; and $R^b$ and $R^c$, at each occurrence, are each independently selected from the group consisting of hydrogen, alkyl, cycloalkyl, heterocycle, heteroaryl, and heteroalkyl.

In certain embodiments, W, X, Y and Z are each $CR^1$; and $R^1$, at each occurrence, is independently selected from the group consisting of hydrogen, $C_1$-$C_3$ alkyl, halogen, $C_1$-$C_3$ alkoxy, cyano, $CFH_2$, $CF_2H$, and $CF_3$.

In certain embodiments, W, X, Y and Z are each $CR^1$; and $R^1$, at each occurrence, is independently selected from the group consisting of hydrogen and halogen.

In certain embodiments, $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^a$, at each occurrence, is independently selected from the group consisting of alkyl, cycloalkyl, heterocycle, heteroaryl, aryl, heteroalkyl, and $NR^bR^c$; and $R^b$ and $R^c$, at each occurrence, are each independently selected from the group consisting of hydrogen, alkyl, cycloalkyl, heterocycle, heteroaryl, and heteroalkyl.

In certain embodiments, $R^2$ is hydrogen, $C_1$-$C_3$ alkyl, $C_2$-$C_4$ alkenyl, $C_3$-$C_6$ cycloalkyl, halogen, $C_1$-$C_3$ alkoxy, $C_3$-$C_6$ cycloalkoxy, cyano, $SO_2R^a$, $NR^bR^c$, hydroxyl, heterocycle, heteroaryl, or $C_1$-$C_3$ haloalkyl; $R^a$, at each occurrence, is independently selected from the group consisting of alkyl, cycloalkyl, heterocycle, heteroaryl, aryl, heteroalkyl, and $NR^bR^c$; and $R^b$ and $R^c$, at each occurrence, are each independently selected from the group consisting of hydrogen, alkyl, cycloalkyl, heterocycle, heteroaryl, and heteroalkyl.

In certain embodiments, $R^2$ is hydrogen, $C_1$-$C_3$ alkyl, $C_2$-$C_4$ alkenyl, $C_3$-$C_6$ cycloalkyl, halogen, $C_1$-$C_3$ alkoxy, $C_3$-$C_6$ cycloalkoxy, cyano, $CFH_2$, $CF_2H$, or $CF_3$.

In certain embodiments, $R^2$ is $C_1$-$C_3$ alkyl, $C_2$-$C_4$ alkenyl, halogen, $C_1$-$C_3$ alkoxy, cyano, or $CF_3$.

In certain embodiments, $R^2$ is $C_1$-$C_3$ alkyl, $C_2$-$C_4$ alkenyl, cyano, or halogen.

In certain embodiments, $R^3$ is alkyl, cycloalkyl, heterocycle, aryl, heteroaryl, $SO_2R^a$, or haloalkyl; $R^a$ is selected from the group consisting of alkyl, cycloalkyl, heterocycle, heteroaryl, aryl, heteroalkyl, and $NR^bR^c$; and $R^b$ and $R^c$ are each independently selected from the group consisting of hydrogen, alkyl, cycloalkyl, heterocycle, heteroaryl, and heteroalkyl.

In certain embodiments, $R^3$ is $C_1$-$C_3$ alkyl, $C_3$-$C_6$ cycloalkyl, heterocycle, aryl, heteroaryl, $SO_2R^a$, $CFH_2$, $CF_2H$, or $CF_3$; $R^a$ is selected from the group consisting of alkyl, cycloalkyl, heterocycle, heteroaryl, aryl, heteroalkyl, and $NR^bR^c$; and $R^b$ and $R^c$ are each independently selected from the group consisting of hydrogen, alkyl, cycloalkyl, heterocycle, heteroaryl, and heteroalkyl.

In certain embodiments, $R^3$ is $C_1$-$C_3$ alkyl, $C_3$-$C_6$ cycloalkyl, heterocycle, aryl, or heteroaryl.

In certain embodiments, $R^3$ is $C_3$-$C_6$ cycloalkyl, aryl, heteroaryl, or heterocycle.

In certain embodiments, $R^3$ is $C_3$-$C_6$ cycloalkyl, aryl, heteroaryl, or heterocycle, with 0-3 substituents independently selected from halogen, cyano, $C_1$-$C_6$ alkyl, $C_1$-$C_6$ fluoroalkyl, $C_1$-$C_6$ alkoxy($C_1$-$C_6$)alkyl, $C_1$-$C_6$ hydroxy($C_1$-$C_6$)alkyl, $C_1$-$C_6$ hydroxy($C_1$-$C_6$)fluoroalkyl, $C_1$-$C_6$ alkoxy($C_1$-$C_6$)fluoroalkyl, $C_1$-$C_6$ cyanoalkyl, $C_1$-$C_6$ cyanofluoroalkyl, $C_3$-$C_8$ cycloalkyl, $C_3$-$C_8$ fluorocycloalkyl, $OR^4$, and $NR^{5a}R^{5b}$; wherein $R^4$ is hydrogen, $C_1$-$C_6$ alkyl or $C_1$-$C_6$ fluoroalkyl; and $R^{5a}$ and $R^{5b}$ are each independently hydrogen, $C_1$-$C_6$ alkyl, $C_3$-$C_8$ cycloalkyl, or $C_1$-$C_6$ heteroalkyl; or $R^{5a}$ and $R^{5b}$ together with the nitrogen atom to which they are attach form a heterocycle.

In certain embodiments, $R^3$ is aryl substituted with 0-3 substituents independently selected from halogen, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl. In certain embodiments, $R^3$ is aryl, wherein aryl is phenyl.

In certain embodiments, $R^3$ is heteroaryl substituted with 0-3 substituents independently selected from halogen, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl.

In certain embodiments, $R^3$ is heteroaryl substituted with 0-3 substituents independently selected from halogen, cyano, $C_1$-$C_3$ alkyl, and $C_1$-$C_3$ fluoroalkyl. In certain embodiments, $R^3$ is heteroaryl substituted with 0-2 substituents independently selected from $C_1$-$C_3$ alkyl, and $C_1$-$C_3$ fluoroalkyl. In certain embodiments, $R^3$ is heteroaryl, wherein heteroaryl is pyridyl. In certain embodiments, $R^3$ is heteroaryl, wherein heteroaryl is pyrazolyl. In certain embodiments, $R^3$ is heteroaryl, wherein heteroaryl is pyrazolyl substituted with 0-2 substituents independently selected from $C_1$-$C_3$ alkyl and $C_1$-$C_3$ fluoroalkyl.

In certain embodiments, $R^3$ is heterocycle substituted with 0-3 substituents independently selected from halogen, cyano, $C_1$-$C_3$ alkyl, $C_1$-$C_3$ fluoroalkyl, $C_1$-$C_3$ alkoxy($C_1$-$C_3$) alkyl, and $OR^4$; wherein $R^4$ is hydrogen, $C_1$-$C_3$ alkyl, or $C_1$-$C_3$ fluoroalkyl. In certain embodiments, $R^3$ is heterocycle, wherein heterocycle is tetrahydrofuranyl.

In certain embodiments, $R^3$ is $C_3$-$C_6$ cycloalkyl substituted with 0-3 substituents independently selected from halogen, cyano, $C_1$-$C_3$ alkyl, $C_1$-$C_3$ fluoroalkyl, $C_1$-$C_3$ alkoxy($C_1$-$C_3$)alkyl, and $OR^4$; wherein $R^4$ is hydrogen, $C_1$-$C_3$ alkyl, or $C_1$-$C_3$ fluoroalkyl. In certain embodiments, $R^3$ is $C_3$-$C_6$ cycloalkyl, wherein $C_3$-$C_6$ cycloalkyl is cyclopentyl.

In certain embodiments, $R^3$ is a monocyclic heteroaryl. In certain embodiments, $R^3$ is a monocyclic heterocycle. In certain embodiments, $R^3$ is an aromatic monocyclic ring. In certain embodiments, $R^3$ is a cycloalkyl. In certain embodiments, $R^3$ is unsubstituted. In certain embodiments, $R^3$ is substituted with 1, 2, 3, 4, or 5 functional groups independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarkylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, anvisulfonyl, aminosulfonyl, sulfinyl, —COOH, ketone, amide, carbamate, and acyl.

In certain embodiments, L is amide, sulfonamide, heteroalkyl, alkoxy, alkoxyalkyl, alkylamino, aminoalkyl, or alkyl.

In certain embodiments, L is —C(O)NR$^d$—, —NR$^d$C(O)—, —OCH$_2$—, —CH$_2$O—, —SO$_2$CH$_2$—, —CH$_2$SO$_2$—, —CH$_2$CH$_2$—, —CH$_2$NR$^d$—, or —NR$^d$CH$_2$—; and R$^d$ is hydrogen or $C_1$-$C_3$ alkyl.

In certain embodiments, L is —C(O)NR$^d$—; and R$^d$ is hydrogen.

In certain embodiments, n is 0, 1, 2 or 3; and t is 0 or 1.

In certain embodiments, n is 0, 1, or 2. In certain embodiments, n is 1, 2, or 3. In certain embodiments, n is 1 or 2. In certain embodiments, n is 2 or 3. In certain embodiments, n is 0 or 1. In certain embodiments, n is 0. In certain embodiments, n is 1. In certain embodiments, n is 2. In certain embodiments, n is 3.

In certain embodiments, t is 0. In certain embodiments, t is 1.

In certain embodiments, $R^4$ and $R^5$ are each independently hydrogen, alkyl, or haloalkyl.

In certain embodiments, $R^4$ and $R^5$ are each independently hydrogen, $C_1$-$C_3$ alkyl, or $C_1$-$C_3$ haloalkyl.

In certain embodiments, $R^4$ and $R^5$ are each independently hydrogen, $C_1$-$C_3$ alkyl, or $CF_3$.

In certain embodiments, $R^4$ and $R^5$ are each independently hydrogen or $C_1$-$C_3$ alkyl.

In certain embodiments, $R^6$ and $R^7$ are each independently selected from the group consisting of hydrogen, alkyl, cycloalkyl, heterocycle, heteroaryl, and haloalkyl.

In certain embodiments, $R^6$ and $R^7$ are each independently selected from the group consisting of hydrogen, $C_1$-$C_3$ alkyl, $C_3$-$C_6$ cycloalkyl, heterocycle, heteroaryl, $CFH_2$, $CF_2H$, and $CF_3$.

In certain embodiments, $R^6$ and $R^7$ are each independently selected from the group consisting of hydrogen, $C_1$-$C_3$ alkyl, and $CF_3$.

In certain embodiments, $R^6$ and $R^7$ together with the nitrogen atom to which they are attached form a heterocycle.

In certain embodiments, $R^4$ and $R^6$ together with the atoms to which they are attached form a heterocycle. In certain embodiments, $R^4$ and $R^6$ together with the atoms to which they are attached form a heterocycle, wherein the heterocycle is a nitrogen containing heterocycle with up to 6 carbon atoms and up to 2 oxygen atoms. In certain embodiments, $R^4$ and $R^6$ together with the atoms to which they are attached form a heterocycle, wherein the heterocycle is an azetidine. In certain embodiments, $R^4$ and $R^6$ together with the atoms to which they are attached form a heterocycle, wherein the heterocycle is a pyrrolidine. In certain embodiments, $R^4$ and $R^6$ together with the atoms to which they are attached form a heterocycle, wherein the heterocycle is a piperidine. In certain embodiments, $R^4$ and $R^6$ together with the atoms to which they are attached form a heterocycle, wherein the heterocycle is a piperazine. In certain embodiments, $R^4$ and $R^6$ together with the atoms to which they are attached form a heterocycle, wherein the heterocycle is a morpholine. In certain embodiments, $R^4$ and $R^6$ together with the atoms to which they are attached form a heterocycle, wherein the heterocycle is an azepane.

In certain embodiments, $R^5$ is hydrogen or $C_1$-$C_3$ alkyl; $R^7$ is hydrogen or $C_1$-$C_3$ alkyl; and $R^4$ and $R^6$ together with the atoms to which they are attached form a heterocycle.

In certain embodiments, $R^5$ is hydrogen or $C_1$-$C_3$ alkyl; $R^7$ is hydrogen or $C_1$-$C_3$ alkyl; and $R^4$ and $R^6$ together with the atoms to which they are attached form a heterocycle, wherein the heterocycle is a nitrogen containing heterocycle with up to 6 carbon atoms and up to 2 oxygen atoms.

In certain embodiments, $R^5$ is hydrogen; $R^7$ is $C_1$-$C_3$ alkyl; and $R^4$ and $R^6$ together with the atoms to which they are attached form a heterocycle, wherein the heterocycle is selected from the group consisting of azetidine, pyrrolidine, piperidine, piperazine, morpholine and azepane.

In certain embodiments, L is —C(O)NR$^d$—; R$^d$ is hydrogen; n is 1; t is 1; $R^5$ is hydrogen or $C_1$-$C_3$ alkyl; $R^7$ is hydrogen or $C_1$-$C_3$ alkyl; and $R^4$ and $R^6$ together with the atoms to which they are attached form a heterocycle.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is $C_1$-$C_3$ alkyl, $C_2$-$C_4$ alkenyl, cyano, or halogen; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is $C_3$-$C_6$ cycloalkyl, aryl, heteroaryl, or heterocycle; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is —$C(O)NR^d$—, —$NR^dC(O)$—, —$OCH_2$—, —$CH_2O$—, —$SO_2CH_2$—, —$CH_2SO_2$—, —$CH_2CH_2$—, —$CH_2NR^d$—, or —$NR^dCH_2$—; $R^d$ is hydrogen or $C_1$-$C_3$ alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and heteroalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is —$C(O)NR^d$—; $R^d$ is hydrogen; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is —$C(O)NR^d$—; $R^d$ is hydrogen; n is 0, 1, 2 or 3; t is 1; $R^5$ is hydrogen or $C_1$-$C_3$ alkyl; $R^7$ is hydrogen or $C_1$-$C_3$ alkyl; and $R^4$ and $R^6$ together with the atoms to which they are attached form a heterocycle;

wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is —C(O)NR$^d$—; $R^d$ is hydrogen; n is 0, 1, 2 or 3; t is 1; $R^5$ is hydrogen or $C_1$-$C_3$ alkyl; $R^7$ is hydrogen or $C_1$-$C_3$ alkyl; and $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is $C_1$-$C_3$ alkyl, $C_2$-$C_4$ alkenyl, cyano, or halogen; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is —C(O)NR$^d$—; $R^d$ is hydrogen; n is 0, 1, 2 or 3; t is 1; $R^5$ is hydrogen or $C_1$-$C_3$ alkyl; $R^7$ is hydrogen or $C_1$-$C_3$ alkyl; and $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is $C_1$-$C_3$ alkyl, $C_2$-$C_4$ alkenyl, cyano, or halogen; $R^3$ is $C_3$-$C_6$ cycloalkyl, aryl, heteroaryl, or heterocycle; L is —C(O)NR$^d$—; $R^d$ is hydrogen; n is 0, 1, 2 or 3; t is 1; $R^5$ is hydrogen or $C_1$-$C_3$ alkyl; $R^7$ is hydrogen or $C_1$-$C_3$ alkyl; and $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is $C_1$-$C_3$ alkyl, $C_2$-$C_4$ alkenyl, cyano, or halogen; $R^3$ is $C_3$-$C_6$ cycloalkyl, aryl, heteroaryl, or heterocycle; L is —C(O)NR$^d$—; $R^d$ is hydrogen; n is 0, 1, 2 or 3; t is 1; $R^5$ is hydrogen or $C_1$-$C_3$ alkyl; $R^7$ is hydrogen or $C_1$-$C_3$ alkyl; and $R^4$ and $R^6$ together with the atoms to which they are attached form a heterocycle; wherein said aryl, heteroaryl, cycloalkyl, and heterocycle, at each occurrence, are independently substituted or unsubstituted with 1, 2, 3, 4, 5, 6, or 7 functional groups independently selected from the group consisting of halogen, =O, =S, cyano, cyanoalkyl, cyanofluoroalkyl, nitro, fluoroalkyl, alkoxyfluoroalkyl, fluoroalkoxy, alkyl, alkenyl, alkynyl, haloalkyl, haloalkoxy, heteroalkyl, cycloalkyl, halocycloalkyl, cycloalkenyl, aryl, heteroaryl, heterocycle, cycloalkylalkyl, heteroarylalkyl, arylalkyl, hydroxy, hydroxyalkyl, hydroxyfluoroalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, aryl sulfonyl, aminosulfonyl, sullinyl, —COOH, ketone, amide, carbamate, and acyl.

In another aspect, the compound of formula (I) is a compound of formula (I-a):

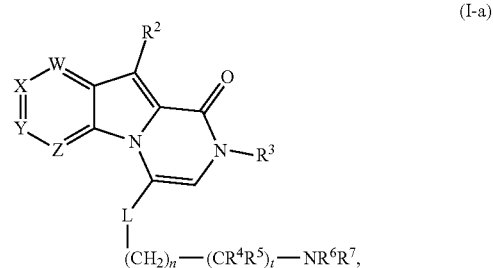

(I-a)

wherein W is $CR^1$ or N; X is $CR^1$ or N; Y is $CR^1$ or N; Z is $CR^1$ or N; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W is $CR^1$ or N; X is $CR^1$ or N; Y is $CR^1$ or N; Z is $CR^1$ or N; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted with 1, 2, 3, 4, 5, 6, or 7 functional groups independently selected from the group consisting of halogen, =O, =S, cyano, cyanoalkyl, cyanofluoroalkyl, nitro, fluoroalkyl, alkoxyfluoroalkyl, fluoroalkoxy, alkyl, alkenyl, alkynyl, haloalkyl, haloalkoxy, heteroalkyl, cycloalkyl, halocycloalkyl, cycloalkenyl, aryl, heteroaryl, heterocycle, eyeloalkylalkyl, heteroarylalkyl, arylalkyl, hydroxy, hydroxyalkyl hydroxyfluoroalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is $C_1$-$C_3$ alkyl, $C_2$-$C_4$ alkenyl, cyano, or halogen; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is $C_3$-$C_6$ cycloalkyl, aryl, heteroaryl, or heterocycle; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is —C(O)$NR^d$, —$NR^d$C(O)—, —OCH$_2$—, —CH$_2$O—, —SO$_2$CH$_2$—, —CH$_2$SO$_2$—, —CH$_2$CH$_2$—, —CH$_2NR^d$—, or —$NR^d$CH$_2$—; $R^d$ is hydrogen or $C_1$-$C_3$ alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is —$C(O)NR^d$—; $R^d$ is hydrogen; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is —$C(O)NR^d$—; $R^d$ is hydrogen; n is 0, 1, 2 or 3; t is 1; $R^5$ is hydrogen or $C_1$-$C_3$ alkyl; $R^7$ is hydrogen or $C_1$-$C_3$ alkyl; and $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is —$C(O)NR^d$—; $R^d$ is hydrogen; n is 0, 1, 2 or 3; t is 1; $R^5$ is hydrogen or $C_1$-$C_3$ alkyl; $R^7$ is hydrogen or $C_1$-$C_3$ alkyl; and $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is $C_1$-$C_3$ alkyl, $C_2$-$C_4$ alkenyl, cyano, or halogen; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is —$C(O)NR^d$—; $R^d$ is hydrogen; n is 0, 1, 2 or 3; t is 1; $R^5$ is hydrogen or $C_1$-$C_3$ alkyl; $R^7$ is hydrogen or $C_1$-$C_3$ alkyl; and $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is $C_1$-$C_3$ alkyl, $C_2$-$C_4$ alkenyl, cyano, or halogen; $R^3$ is $C_3$-$C_6$ cycloalkyl, aryl, heteroaryl, or heterocycle; L is —$C(O)NR^d$—; $R^d$ is hydrogen; n is 0, 1, 2 or 3; t is 1; $R^5$ is hydrogen or $C_1$-$C_3$ alkyl; $R^7$ is hydrogen or $C_1$-$C_3$ alkyl; and $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is $C_1$-$C_3$ alkyl, $C_2$-$C_4$ alkenyl, cyano, or halogen; $R^3$ is $C_3$-$C_6$ cycloalkyl, aryl, heteroaryl, or heterocycle; L is —$C(O)NR^d$—; $R^d$ is hydrogen; n is 0, 1, 2 or 3; t is 1; $R^5$ is hydrogen or $C_1$-$C_3$ alkyl; $R^7$ is hydrogen or $C_1$-$C_3$ alkyl; and $R^4$ and $R^6$ together with the atoms to which they are attached form a heterocycle; wherein said aryl, heteroaryl, cycloalkyl, and heterocycle, at each occurrence, are independently substituted or unsubstituted with 1, 2, 3, 4, 5, 6, or 7 functional groups independently selected from the group consisting of halogen, =O, =S, cyano, cyanoalkyl, cyanofluoroalkyl, nitro, fluoroalkyl, alkoxyfluoroalkyl, fluoroalkoxy, alkyl, alkenyl, alkynyl, haloalkyl, haloalkoxy, heteroalkyl, cycloalkyl, halocycloalkyl, cycloalkenyl, aryl, heteroaryl, heterocycle, cycloalkylalkyl, heteroarylalkyl, hydroxy, hydroxyalkyl, hydroxyfluoroalkyl, alkoxy, alkoxyalkyl, alkylene, aryloxy, phenoxy, benzyloxy, amino, alkylamino, acylamino, aminoalkyl, acylamino, sulfonylamino, sulfinylamino, sulfonyl, alkylsulfonyl, arylsulfonyl, aminosulfonyl, sulfinyl, —COOH, ketone, amide, carbamate, and acyl.

In another aspect, the compound of formula (I) is a compound of formula (I-b):

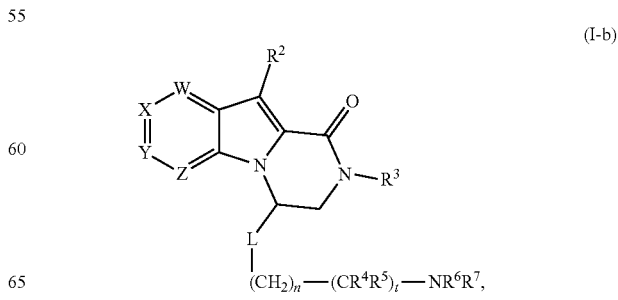

(I-b)

wherein W is $CR^1$ or N; X is $CR^1$ or N; Y is $CR^1$ or N; Z is $CR^1$ or N; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W is $CR^1$ or N; X is $CR^1$ or N; Y is $CR^1$ or N; Z is $CR^1$ or N; $R^1$, at each occurrence, is independently selected from the group consisting of hydrogen, alkyl, alkenyl, cycloalkyl, halogen, alkoxy, cycloalkoxy, heteroalkykl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted with 1, 2, 3, 4, 5, 6, or 7 functional groups independently selected from the group consisting of halogen, —O, —S, cyano, cyanoalkyl, cyanofluoroalkyl, nitro, fluoroalkyl, alkoxyfluoroalkyl, fluoroalkoxy, alkyl, alkenyl, alkynyl, haloalkyl, haloalkoxy, heteroalkyl, cycloalkyl, halocycloalkyl, cycloalkenyl, aryl, heteroaryl, heterocycle, cycloalkylalkyl, heteroarylalkyl, arylalkyl, hydroxy, hydroxyalkyl, hydroxyfluoroalkyl, alkoxy, alkoxyalkyl, alkylene, aryloxy, phenoxy, benzyloxy, amino, alkylamino, acylamino, aminoalkyl, arylamino, sulfonyl amino, sulfinylamino, sulfonyl, alkylsulfonyl, aryl sulfonyl, aminosulfonyl, sulfinyl, —COOH, ketone, amide, carbamate, and acyl.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is $C_1$-$C_3$ alkyl, $C_2$-$C_4$ alkenyl, cyano, or halogen; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle;

or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is $C_3$-$C_6$ cycloalkyl, aryl, heteroaryl, or heterocycle; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is amide, sulfonamide, heteroalkyl, alkoxy, alkoxyalkyl, alkylamino, aminoalkyl, or alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence are each independently selected from the group consisting of hydrogen, alkyl, cycloalkyl, heterocycle, heteroaryl, and heteroalkyl; L is —$C(O)NR^d$—, —$NR^dC(O)$—, —$OCH_2$—, —$CH_2O$—, —$SO_2CH_2$—, —$CH_2SO_2$—, —$CH_2CH_2$—, —$CH_2NR^d$—, or —$NR^dCH_2$—; $R^d$ is hydrogen or $C_1$-$C_3$ alkyl; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is —$C(O)NR^d$—; $R^d$ is hydrogen; n is 0, 1, 2 or 3; t is 0 or 1; $R^4$ and $R^5$ are each independently hydrogen, alkyl, or haloalkyl; and $R^6$ and $R^7$ are each independently selected from the group consisting of hydrogen, alkyl, cycloalkyl, heterocycle, heteroaryl, and haloalkyl; or $R^6$ and $R^7$ together with the nitrogen atom to which they are attached form a heterocycle; or $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is —$C(O)NR^d$—; $R^d$ is hydrogen; n is 0, 1, 2 or 3; t is 1; $R^5$ is hydrogen or $C_1$-$C_3$ alkyl; $R^7$ is hydrogen or $C_1$-$C_3$ alkyl; and $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is —$C(O)NR^d$—; $R^d$ is hydrogen; n is 0, 1, 2 or 3; t is 1; $R^5$ is hydrogen or $C_1$-$C_3$ alkyl; $R^7$ is hydrogen or $C_1$-$C_3$ alkyl; and $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is $C_1$-$C_3$ alkyl, $C_2$-$C_4$ alkenyl, cyano, or halogen; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; L is —$C(O)NR^d$—; $R^d$ is hydrogen; n is 0, 1, 2 or 3; t is 1; $R^5$ is hydrogen or $C_1$-$C_3$ alkyl; $R^7$ is hydrogen or $C_1$-$C_3$ alkyl; and $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is $C_1$-$C_3$ alkyl, $C_2$-$C_4$ alkenyl, cyano, or halogen; $R^3$ is $C_3$-$C_6$ cycloalkyl, aryl, heteroaryl, or heterocycle; L is —C(O)$NR^d$—; $R^d$ is hydrogen; n is 0, 1, 2 or 3; t is 1; $R^5$ is hydrogen or $C_1$-$C_3$ alkyl; $R^7$ is hydrogen or $C_1$-$C_3$ alkyl; and $R^4$ and $R^6$ together with the atoms to which they are attached form a heterocycle; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is $C_1$-$C_3$ alkyl, $C_2$-$C_4$ alkenyl, cyano, or halogen; $R^3$ is $C_3$-$C_6$ cycloalkyl, aryl, heteroaryl, or heterocycle; L is —C(O)$NR^d$—; $R^d$ is hydrogen; n is 0, 1, 2 or 3; t is 1; $R^5$ is hydrogen or $C_1$-$C_3$ alkyl; $R^7$ is hydrogen or $C_1$-$C_3$ alkyl; and $R^4$ and $R^6$ together with the atoms to which they are attached form a heterocycle; wherein said aryl, heteroaryl, cycloalkyl, and heterocycle, at each occurrence, are independently substituted or unsubstituted with 1, 2, 3, 4, 5, 6, or 7 functional groups independently selected from the group consisting of halogen, =O, =S, cyano, cyanoalkyl, cyanofluoroalkyl, nitro, fluoroalkyl, alkoxyfluoroalkyl, fluoroalkoxy, alkyl, alkenyl, alkynyl, haloalkyl, haloalkoxy, heteroalkyl, cycloalkyl, halocycloalkyl, cycloalkenyl, aryl, heteroaryl, heterocycle, cycloalkylalkyl, heteroarylalkyl, arylalkyl, hydroxy, hydroxyalkyl, hydroxyfluoroalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

In another aspect, the compound of formula (I) is a compound of formula (I-c):

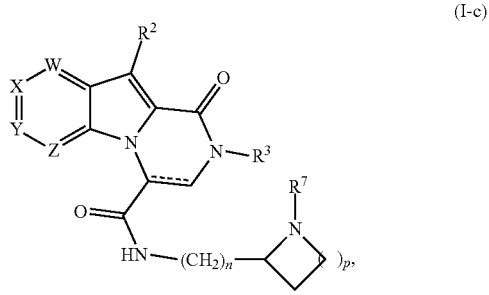

(I-c)

wherein W is $CR^1$ or N; X is $CR^1$ or N; Y is $CR^1$ or N; Z is $CR^1$ or N; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, C(O)$NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; n is 0, 1, 2 or 3; p is 1, 2, 3 or 4; $R^7$ is selected from the group consisting of hydrogen, alkyl, cycloalkyl, heterocycle, heteroaryl, and haloalkyl; wherein said aryl, heteroaryl, cycloalkyl, and heterocycle, at each occurrence, are independently substituted or unsubstituted.

In certain embodiments, W is $CR^1$ or N; X is $CR^1$ or N; Y is $CR^1$ or N; Z is $CR^1$ or N; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, C(O)$NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; n is 0, 1, 2 or 3; p is 1, 2, 3 or 4; $R^7$ is selected from the group consisting of hydrogen, alkyl, cycloalkyl, heterocycle, heteroaryl, and haloalkyl; wherein said aryl, heteroaryl, cycloalkyl, and heterocycle, at each occurrence, are independently substituted or unsubstituted with 1, 2, 3, 4, 5, 6, or 7 functional groups independently selected from the group consisting of halogen, =O, =S, cyano, cyanoalkyl, cyanofluoroalkyl, nitro, fluoroalkyl, alkoxyfluoroalkyl, fluoroalkoxy, alkyl, alkenyl, alkynyl, haloalkyl, haloalkoxy, heteroalkyl, cycloalkyl, halocycloalkyl, cycloalkenyl, aryl, heteroaryl, heterocycle, cycloalkylalkyl, heteroarylalkyl, arylalkyl, hydroxy, hydroxyalkyl, hydroxyfluoroalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, C(O)$NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; n is 0, 1, 2 or 3; p is 1, 2, 3 or 4; $R^7$ is selected from the group consisting of hydrogen, alkyl, cycloalkyl, heterocycle, heteroaryl, and haloalkyl; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; n is 0, 1, 2 or 3; p is 1, 2, 3 or 4; $R^7$ is selected from the group consisting of hydrogen, alkyl, cycloalkyl, heterocycle, heteroaryl, and haloalkyl; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is $C_1$-$C_3$ alkyl, $C_2$-$C_4$ alkenyl, cyano, or halogen; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; n is 0, 1, 2 or 3; p is 1, 2, 3 or 4; $R^7$ is selected from the group consisting of hydrogen, alkyl, cycloalkyl, heterocycle, heteroaryl, and haloalkyl; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is $C_3$-$C_6$ cycloalkyl, aryl, heteroaryl, or heterocycle; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; n is 0, 1, 2 or 3; p is 1, 2, 3 or 4; $R^7$ is independently selected from the group consisting of hydrogen, alkyl, cycloalkyl, heterocycle, heteroaryl, and haloalkyl; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; n is 0, 1, 2 or 3; p is 1, 2, 3 or 4; $R^7$ is selected from the group consisting of hydrogen, alkyl, cycloalkyl, heterocycle, heteroaryl, and haloalkyl; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; n is 0, 1, 2 or 3; p is 1, 2, 3 or 4; $R^7$ is selected from the group consisting of hydrogen, alkyl, cycloalkyl, heterocycle, heteroaryl, and haloalkyl; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen, alkyl, alkenyl, cycloalkyl, halogen, alkoxy, cycloalkoxy, heteroalkyl, cyano, $SO_2R^a$, $NR^bR^c$, $C(O)NR^bR^c$, hydroxyl, heterocycle, heteroaryl, and haloalkyl; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; n is 0, 1, 2 or 3; p is 1, 2, 3 or 4; $R^7$ is hydrogen or $C_1$-$C_3$ alkyl; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; n is 0, 1, 2 or 3; p is 1, 2, 3 or 4; $R^7$ is hydrogen or $C_1$-$C_3$ alkyl; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is $C_1$-$C_3$ alkyl, $C_2$-$C_4$ alkenyl, cyano, or halogen; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; n is 0, 1, 2 or 3; p is 1, 2, 3 or 4; $R^7$ is hydrogen or $C_1$-$C_3$ alkyl; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is $C_1$-$C_3$ alkyl, $C_2$-$C_4$ alkenyl, cyano, or halogen; $R^3$ is $C_3$-$C_6$ cycloalkyl, aryl, heteroaryl, or heterocycle; n is 0, 1, 2 or 3; p is 1, 2, 3 or 4; $R^7$ is hydrogen or $C_1$-$C_3$ alkyl; wherein said aryl, heteroaryl, cycloalkyl, and heterocycle, at each occurrence, are independently substituted or unsubstituted.

In certain embodiments, W, X, Y and Z are each $CR^1$; $R^1$, at each occurrence, is independently selected from the group consisting of hydrogen and halogen; $R^2$ is $C_1$-$C_3$ alkyl, $C_2$-$C_4$ alkenyl, cyano, or halogen; $R^3$ is $C_3$-$C_6$ cycloalkyl, aryl, heteroaryl, or heterocycle; n is 0, 1, 2 or 3; p is 1, 2, 3 or 4; $R^7$ is hydrogen or $C_1$-$C_3$ alkyl; wherein said aryl, heteroaryl, cycloalkyl, and heterocycle, at each occurrence, are independently substituted or unsubstituted with 1, 2, 3, 4, 5, 6, or 7 functional groups independently selected from the group consisting of halogen, =O, =S, cyano, cyanoalkyl, cyanofluoroalkyl, nitro, fluoroalkyl, alkoxyfluoroalkyl, fluoroalkoxy, alkyl, alkenyl, alkynyl, haloalkyl, haloalkoxy, heteroalkyl, cycloalkyl, halocycloalkyl, cycloalkenyl, aryl, heteroaryl, heterocycle, cycloalkylalkyl, heteroarylalkyl, arylalkyl, hydroxy, hydroxyalkyl, hydroxyfluoroalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfonyl, —COOH, ketone, amide, carbamate, and acyl.

In certain embodiments, p is 1, 2, 3 or 4. In certain embodiments, p is 1, 2 or 3. In certain embodiments, p is 2, 3 or 4. In certain embodiments, p is 1 or 2. In certain embodiments, p is 2 or 3. In certain embodiments, p is 3 or 4. In certain embodiments, p is 1. In certain embodiments, p is 2. In certain embodiments, p is 3. In certain embodiments, p is 4.

In another aspect, the compound of formula (I) is a compound of formula (I-d), (I-d'), (I-e), (I-e'), (I-f), or (I-f'):

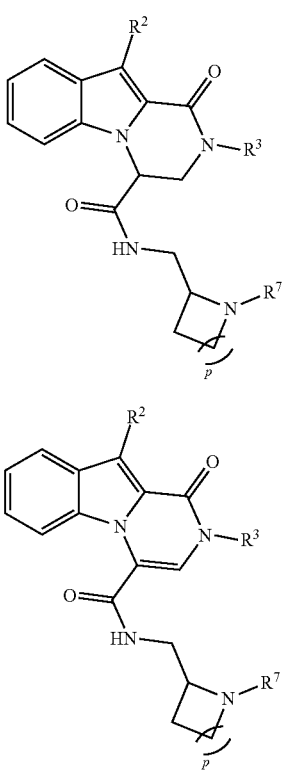

(I-d)

(I-d')

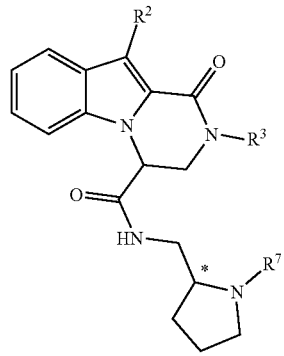

(I-e)

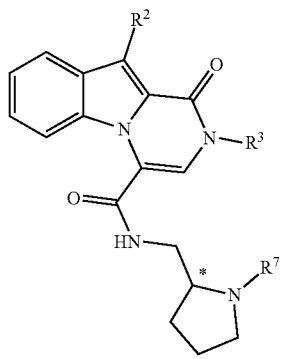

(I-e')

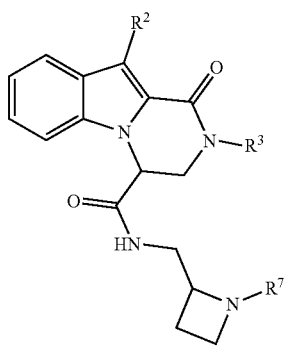

(I-f)

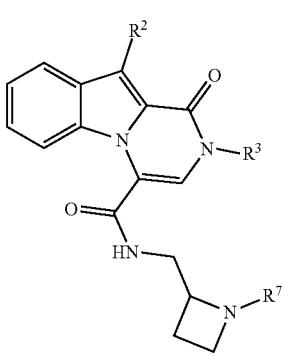

(I-f')

wherein $R^2$ is hydrogen, alkyl, alkenyl, cycloalkyl, halogen, alkoxy, cycloalkoxy, heteroalkyl, cyano, $SO_2R^a$, $NR^bR^c$, hydroxyl, heterocycle, heteroaryl or haloalkyl; $R^3$ is alkyl, cycloalkyl, heterocycle, aryl, heteroaryl, $SO_2R^a$, or haloalkyl; $R^a$, at each occurrence, is independently selected from the group consisting of alkyl, cycloalkyl, heterocycle, heteroaryl, aryl, heteroalkyl, and $NR^bR^c$; $R^b$ and $R^c$, at each occurrence, are each independently selected from the group consisting of hydrogen, alkyl, cycloalkyl, heterocycle, heteroaryl, and heteroalkyl; $R^7$ is independently selected from the group consisting of hydrogen, alkyl, cycloalkyl, heterocycle, heteroaryl, and haloalkyl; wherein said aryl, heteroaryl, cycloalkyl, and heterocycle, at each occurrence, are independently substituted or unsubstituted; and p, when present, is 1, 2, 3, or 4. In certain embodiments, $R^2$ is $C_1$-$C_6$-alkyl, $C_2$-$C_6$-alkenyl, halogen, or cyano; $R^3$ is cycloalkyl, heterocycle, aryl, or heteroaryl; $R^7$ is hydrogen or $C_1$-$C_6$-alkyl; and p, when present, is 1, 2, or 3. In certain embodiments, $R^2$ is methyl, vinyl, fluoro, chloro, bromo, or cyano; $R^3$ is substituted or unsubstituted cyclopentyl, tetrahydrofuranyl, phenyl, pyridinyl, or pyrazolyl; $R^7$ is hydrogen or isopropyl; p, when present, is 1, or 2; and * denotes a stereocenter. In certain embodiments, the carbon atom * adjacent the pyrrolidinyl nitrogen has the (S)-configuration. In certain embodiments, the carbon atom * adjacent the pyrrolidinyl nitrogen has the (R)-configuration.

Representative compounds of formula (I) include, but are not limited to:

(S)-2-cyclopentyl-N-((1-isopropylpyrrolidin-2-yl)methyl)-10-methyl-1-oxo-1,2-dihydropyrazino[1,2-a]indole-4-carboxamide;
(R)-2-cyclopentyl-N-((1-isopropylpyrrolidin-2-yl)methyl)-10-methyl-1-oxo-1,2-dihydropyrazino[1,2-a]indole-4-carboxamide;
2-cyclopentyl-N—(((S)-1-isopropylpyrrolidin-2-yl)methyl)-10-methyl-1-oxo-1,2,3,4-tetrahydropyrazino[1,2-a]indole-4-carboxamide;
N—(((S)-1-isopropylpyrrolidin-2-yl)methyl)-10-methyl-1-oxo-2-((S)-tetrahydrofuran-3-yl)-1,2-dihydropyrazino[1,2-a]indole-4-carboxamide;
N—(((R)-1-isopropylpyrrolidin-2-yl)methyl)-10-methyl-1-oxo-2-((S)-tetrahydrofuran-3-yl)-1,2-dihydropyrazino[1,2-a]indole-4-carboxamide;
(S)-2-cyclopentyl-8-fluoro-N-((1-isopropylpyrrolidin-2-yl)methyl)-10-methyl-1-oxo-1,2-dihydropyrazino[1,2-a]indole-4-carboxamide;
(R)-2-cyclopentyl-8-fluoro-N-((1-isopropylpyrrolidin-2-yl)methyl)-10-methyl-1-oxo-1,2-dihydropyrazino[1,2-a]indole-4-carboxamide;
(R)-2-cyclopentyl-N—(((S)-1-isopropylpyrrolidin-2-yl)methyl)-10-methyl-1-oxo-1,2,3,4-tetrahydropyrazino[1,2-a]indole-4-carboxamide;
(S)-2-cyclopentyl-N—(((S)-1-isopropylpyrrolidin-2-yl)methyl)-10-methyl-1-oxo-1,2,3,4-tetrahydropyrazino[1,2-a]indole-4-carboxamide;
(S)-10-chloro-2-cyclopentyl-N-((1-isopropylpyrrolidin-2-yl)methyl)-1-oxo-1,2-dihydropyrazino[1,2-a]indole-4-carboxamide;
(R)-10-chloro-2-cyclopentyl-N-((1-isopropylpyrrolidin-2-yl)methyl)-1-oxo-1,2-dihydropyrazino[1,2-a]indole-4-carboxamide;
(S)-10-bromo-2-cyclopentyl-N-((1-isopropylpyrrolidin-2-yl)methyl)-1-oxo-1,2-dihydropyrazino[1,2-a]indole-4-carboxamide;
(R)-10-bromo-2-cyclopentyl-N-((1-isopropylpyrrolidin-2-yl)methyl)-1-oxo-1,2-dihydropyrazino[1,2-a]indole-4-carboxamide;
(R)—N-((1-isopropylpyrrolidin-2-yl)methyl)-10-methyl-1-oxo-2-phenyl-1,2-dihydropyrazino[1,2-a]indole-4-carboxamide;
(S)-10-cyano-2-cyclopentyl-N-((1-isopropylpyrrolidin-2-yl)methyl)-1-oxo-1,2-dihydropyrazino[1,2-a]indole-4-carboxamide;
(S)-2-cyclopentyl-N-((1-isopropylpyrrolidin-2-yl)methyl)-1-oxo-10-vinyl-1,2-dihydropyrazino[1,2-a]indole-4-carboxamide;
(S)—N-((1-isopropylpyrrolidin-2-yl)methyl)-10-methyl-2-(1-methyl-1H-pyrazol-4-yl)-1-oxo-1,2-dihydropyrazino[1,2-a]indole-4-carboxamide;
(R)—N-((1-isopropylpyrrolidin-2-yl)methyl)-10-methyl-2-(1-methyl-1H-pyrazol-4-yl)-1-oxo-1,2-dihydropyrazino[1,2-a]indole-4-carboxamide;
(S)—N-((1-isopropylpyrrolidin-2-yl)methyl)-10-methyl-1-oxo-2-(pyridin-3-yl)-1,2-dihydropyrazino[1,2-a]indole-4-carboxamide;
(R)—N-((1-isopropylpyrrolidin-2-yl)methyl)-10-methyl-1-oxo-2-(pyridin-3-yl)-1,2-dihydropyrazino[1,2-a]indole-4-carboxamide;
N-(azetidin-2-ylmethyl)-2-cyclopentyl-10-methyl-1-oxo-1,2-dihydropyrazino[1,2-a]indole-4-carboxamide; and
2-cyclopentyl-N-((1-isopropylazetidin-2-yl)methyl)-10-methyl-1-oxo-1,2-dihydropyrazino[1,2-a]indole-4-carboxamide; or pharmaceutically acceptable salt thereof.

Compound names are assigned by using Struct=Name naming algorithm as part of CHEMDRAW® ULTRA v. 12.0.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

A. Allosteric Modulation and Agonism of the GLP-1 Receptor

The disclosed compounds may act or function as positive allosteric modulators (PAM), allosteric agonists, or ago-positive allosteric modulators (ago-PAM) of the GLP-1 receptor.

Compounds of formula (I) can activate the GLP-1 receptor with an $EC_{50}$ ranging from about 1 nM to about 30 μM. The compounds may have an $EC_{50}$ of about 30 μM, about 29 μM, about 28 μM, about 27 μM, about 26 μM, about 25 μM, about 24 μM, about 23 μM, about 22 μM, about 21 μM, about 20 μM, about 19 μM, about 18 μM, about 17 μM, about 16 μM, about 15 μM, about 14 μM, about 13 μM, about 12 μM, about 11 μM, about 10 μM, about 9 μM, about 8 μM, about 7 μM, about 6 μM, about 5 μM, about 4 μM, about 3 μM, about 2 μM, about 1 μM, about 950 nM, about 900 nM, about 850 nM, about 800 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 50 nM, about 10 nM, about 5 nM, or about 1 nM. Compounds of formula (I) can activate the GLP-1 receptor with an $EC_{50}$ of less than 30 μM, less than 29 μM, less than 28 μM, less than 27 μM, less than 26 μM, less than 25 μM, less than 24 μM, less than 23 μM, less than 22 μM, less than 21 μM, less than 20 μM, less than 19 μM, less than 18 μM, less than 17 μM, less than 16 μM, less than 15 μM, less than 14 μM, less than 13 μM, less than 12 μM, less than 11 μM, less than 10 μM, less than 9 μM, less than 8 μM, less than 7 μM, less than 6 μM, less than 5 μM, less than 4 μM, less than 3 μM, less than 2 μM, less than 1 μM, less than 950 nM, less than 900 nM, less than 850 nM, less than 800 nM, less than 850 nM, less than 800 nM, less than 750 nM, less than 700 nM, less than 650 nM, less than 600 nM, less than 550 nM, less than 500 nM, less than 450 nM, less than 400 nM, less than 350 nM, less than 300 nM, less than 250 nM, less than 200 nM, less than 150 nM, less than 100 nM, less than 50 nM, less than 10 nM, less than 5 nM, or less than 1 nM.

Compounds of formula (I) may be selective modulators of the GLP-1 receptor.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

B. General Synthesis

Compounds of formula (I) may be prepared by synthetic processes or by metabolic processes. Preparation of the compounds by metabolic processes includes those occurring in the human or animal body (in vivo) or processes occurring in vitro.

Abbreviations which have been used in the descriptions of the Schemes that follow are: T3P is propane phosphonic acid anhydride; HATU is 1-[bis(dimethylamino)methylene]-1H-1,2,3-triazolo[4,5-b]pyridinium 3-oxid hexafluorophosphate; DIEA is N,N-diisopropylethylamine; NMO is N-methylmorpholine N-oxide; THF is tetrahydrofuran; DMF is dimethylformamide; TEA is triethylamine; and DCM is dichloromethane.

Compounds of formula (I) can be synthesized as shown in Schemes 1 and 2.

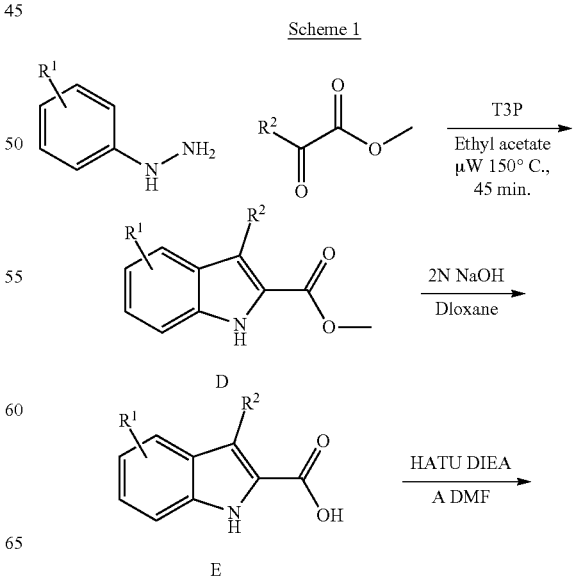

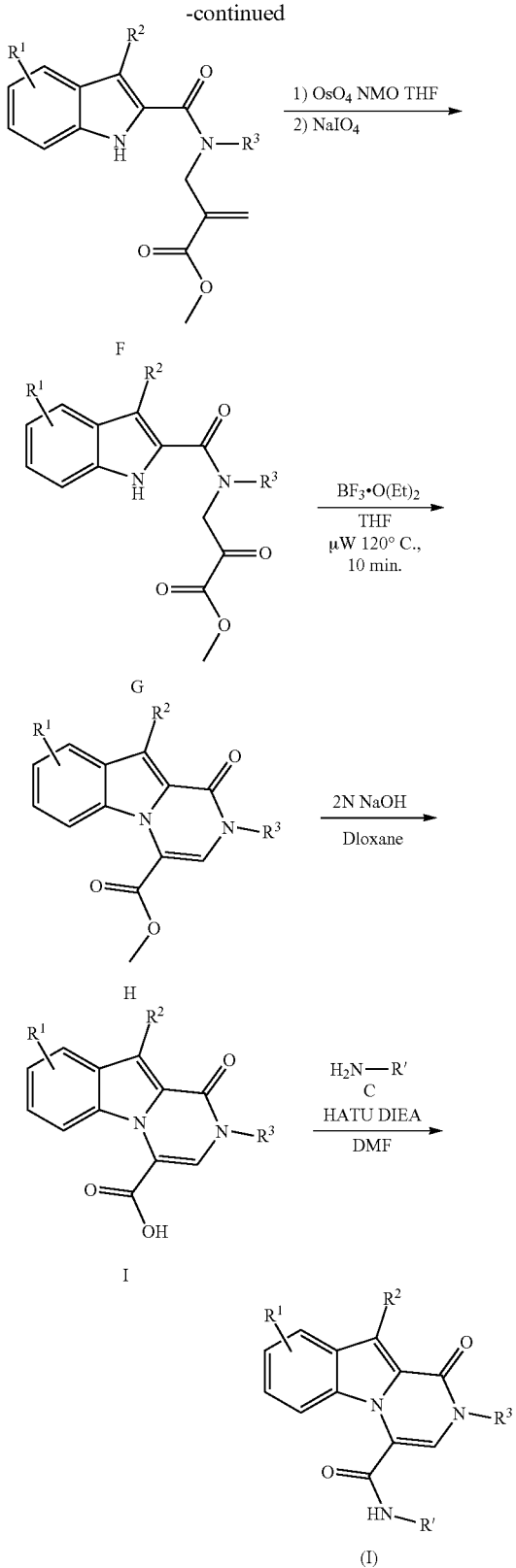

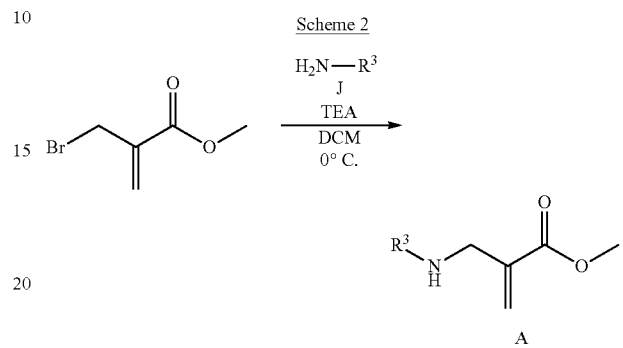

with osmium tetroxide followed by sodium periodate can provide compound G. Intramolecular cyclization to compound H can be affected with a Lewis acid (e.g., boron trifluoride diethyl etherate). Hydrolysis of the pendant ester can provide carboxylic acid compound I, which can undergo coupling with amine compound C to provide a compound of formula (I), where R' is —$(CH_2)_n$—$(CR^4R^5)_t$—$NR^6R^7$.

Compounds of formula A can be prepared as shown in Scheme 2. Methyl 2-(bromomethyl) acrylate can undergo substitution with amine compound J to provide a compound A.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods As shown in Scheme 1, reaction of a phenylhydrazine and an alpha-ketoester can provide a compound D. After hydrolysis to compound E, the carboxylic acid can be coupled with amine compound A to provide compound F. Treatment described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

3. Pharmaceutical Compositions

The disclosed compounds may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention [e.g., a compound of formula (I)] are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active [e.g., compound of formula (I)] and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound [e.g., a compound of formula (I)], and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound [e.g., a compound of formula (I)], and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

4. Methods of Treatment

The disclosed compounds and compositions may be used in methods for treatment of GLP-1 related medical disorders and/or diseases. The methods of treatment may comprise administering to a subject in need of such treatment a composition comprising a therapeutically effective amount of the compound of formula (I).

The compositions can be administered to a subject in need thereof to modulate GLP1R, for a variety of diverse biological processes. The present disclosure is directed to methods for administering the composition to modulate GLP1R, a GPCR that is expressed in pancreatic beta cells, pancreatic alpha cells, neurons in the central nervous system, and a variety of other tissues and cells. Activated GLP1R stimulates the adenylyl cyclase pathway, which results in increased insulin synthesis and release of insulin, for example.

The compositions may be useful for treating and preventing certain diseases and disorders in humans and animals related to the GLP-1 axis. Treatment or prevention of such diseases and disorders can be effected by modulating GLP1R in a subject, by administering a compound or composition of the invention, either alone or in combination with another active agent as part of a therapeutic regimen to a subject in need thereof.

The compositions may be useful for treating a disease or disorder associated with GLP-1, wherein the disease or disorder is selected from at least one of diabetes mellitus type 2, obesity, depression, Alzheimer's disease, Parkinson's disease, Huntington's disease, stroke, cognitive dysfunction, learning disability, and asthma.

a. Type 2 Diabetes

The compositions may be useful for treating or preventing Type 2 diabetes. GLP-1 is synthesized and processed in enteroendocrine L cells in the gut and is released into the local circulation upon nutrient ingestion. It has numerous salutary effects throughout the body by activating its group B GPCR. GLP1Rs are expressed in pancreatic β cells where GLP-1 action substantially amplifies insulin secretion. Glucagon over-secretion is an increasingly recognized pathophysiological feature of diabetes, and GLP-1 via GLP1R suppresses glucagon release from α cells. From a safety perspective, GLP-1 does not increase insulin secretion under euglycemic conditions, nor does it suppress glucagon secretion under hypoglycemic conditions. Thus, diabetes therapeutics that capitalize on the GLP-1 axis have a low risk of hypoglycemia and a significant safety advantage. Accordingly, activation of the GLP1R with the positive allosteric modulators of GLP1R may be an effective treatment of Type 2 diabetes.

b. Obesity

The compositions may be useful for treating or preventing obesity. See, e.g., Neff, L. M., Kushner, R. F., Emerging role of GLP-1 receptor agonists in the treatment of obesity. Diabetes, Metabolic Syndrome and Obesity: Targets and Therapy, 2010, 3, 263-273; and Hurtado, V., Roncero, I., Blazquez, E., Alvarez, E., Sanz, C., Glucagon-Like Peptide-1 and Its Implications in Obesity, in Hot Topics in Endocrine and Edocrine-related diseases, Chapter 7, 2013. GLP-1 has diverse biological activities in both peripheral tissues and the central nervous system. GLP-1 stimulates pancreas insulin secretion in a glucose-dependent manner after a meal, thus referred to as an "incretin"; moreover, GLP-1 is also considered an anorexigenic peptide, reducing appetite and feeding by activation of the GLP1R in human hypothalamus and brain stem (Knudsen et al., The arcuate nucleus mediates GLP-1 receptor agonist liraglutide-dependent weight loss. J. Clin. Invest. 2014, 124(10):4473-4488). Thus, GLP-1 is an antidiabetogenic agent due to its action in the pancreas while acting in hypothalamic areas, helping to generate a state of satiety, and this has been validated in rodents, reducing food intake and inducing weight loss. Indeed, one GLP-1 peptide analogue (liraglutide) is FDA approved for the treatment of obesity.

The compositions may be useful for treating or preventing antipsychotic weight gain. See, e.g., Sharma, A. N., Ligade, S. S., Sharma, J. N., Shukla, P., Elased, K. M., Lucot, J. B., GLP-1 receptor agonist liraglutide reverses long-term atypical antipsychotic treatment associated behavioral depression and metabolic abnormalities in rats. Metab. Brain Dis. 2015 April, 30(2):519-27.

c. Depression

The compositions may be useful for treating or preventing depression. See, e.g., Sharma, A. N., Ligade, S. S., Sharma, J. N., Shukla, P., Elased, K. M., Lucot, J. B., GLP-1 receptor agonist liraglutide reverses long-term atypical antipsychotic treatment associated behavioral depression and metabolic abnormalities in rats. Metab. Brain Dis. 2015 April, 30(2): 519-27; and McIntyre R S, Powell A M, Kaidanovich-Beilin O, Soczynska J K, Alsuwaidan M, Woldeyohannes H O, Kim A S, Gallaugher L A, The neuroprotective effects of GLP-1: possible treatments for cognitive deficits in individuals with mood disorders. Behav. Brain Res. 2013 Jan. 15, 237:164-71.

d. Alzheimer's Disease

The compositions may be useful for treating or preventing Alzheimer's disease. See, e.g., Christian Hölscher, Central effects of GLP-1: new opportunities for treatments of neurodegenerative diseases. J. Endocrinol. Apr. 1, 2014 221 T31-T41. In preclinical studies of Alzheimer's disease (AD), Parkinson's disease (PD), stroke and other neurodegenerative disorders, it has been shown that most GLP-1 mimetics cross the bloodbrain barrier (though limited) and show impressive neuroprotective effects in numerous studies. In animal models of AD, GLP-1 mimetics such as exendin-4, liraglutide and lixisenatide have shown protective effects in the CNS by reducing (β-amyloid plaques, preventing loss of synapses and memory impairments, and reducing oxidative stress and the chronic inflammatory response in the brain. These encouraging findings have spawned several clinical trials, some of which have shown encouraging initial results. Therefore, GLP-1 mimetics show great promise as a novel treatment for neurodegenerative conditions.

e. Parkinson's Disease

The compositions may be useful for treating or preventing Parkinson's disease. See, e.g., Christian Hölscher, Central effects of GLP-1: new opportunities for treatments of neurodegenerative diseases. J. Endocrinol. Apr. 1, 2014 221 T31-T41; and Morris, L. C., Nance, K. D., Gentry, P. R., Days, E. L., Weaver, C. D., Niswender, C. M., Thompson, A. D., Jones, C. K., Locuson, C. W., Morrison, R. D., Daniels, J. S., Niswender, K. D., Lindsley, C. W., Discovery of (S)-2-cyclopentyl-N-((1-isopropylpyrrolidin2-yl)-9-methyl-1-oxo-2,9-dihydro-1H-pyrrido[3,4-b]indole-4-carboxamide (VU0453379): a novel, CNS penetrant GLP-1 positive allosteric modulator (PAM). J. Med. Chem. 2014, 57, 10192-10197.

In animal models of PD, exendin-4 showed protection of dopaminergic neurons in the substantia nigra and prevention of dopamine loss in the basal ganglia while preserving motor control. An early GLP-1 PAM reversed haloperdiol induced catalepsy, a standard preclinical model of PD with translation to the clinic.

f. Huntington's Disease

The compositions may be useful for treating or preventing Huntington's disease. See, e.g., Christian Hölscher, Central effects of GLP-1: new opportunities for treatments of neurodegenerative diseases. J. Endocrinol. Apr. 1, 2014 221 T31-T41.

g. Stroke

The compositions may be useful for treating or preventing stroke. See, e.g., Darsalia V, Nathanson D, Nyström T, Klein T, Sjöholm Å, Patrone C., GLP-1R activation for the treatment of stroke: updating and future perspectives. Rev. Endocr. Metab. Disord. 2014 September, 15(3):233-42; and Vladimer Darsalia, Shiva Mansouri, Henrik Ortsäter, Anna Olverling, Nino Nozadze, Camilla Kappe, Kerstin Iverfeldt, Linda M. Tracy, Nina Grankvist, Åke Sjöholm, and Cesare Patrone, Glucagon-like peptide-1 receptor activation reduces ischaemic brain damage following stroke in Type 2 diabetic rats. Clin. Sci. (Lond). 2012 May 1, 122 (Pt 10): 473-483. Results show a pronounced anti-stroke, neuroprotective and anti-inflammatory effect of peripheral and chronic Ex-4 treatment in middle-aged diabetic animals in a preclinical setting that has the potential to mimic the clinical treatment.

h. Cognitive Dysfunction

The compositions may be useful for treating or preventing cognitive dysfunction. See, e.g., Christian Hölscher, Central effects of GLP-1: new opportunities for treatments of neurodegenerative diseases. J. Endocrinol. Apr. 1, 2014 221 T31-T41; and Roger S. McIntyre, Alissa M. Powell, Oksana Kaidanovich-Beilin, Joanna K. Soczynska, Mohammad Alsuwaidan, Hanna O. Woldeyohannes, Ashley S. Kim, L. Ashley Gallaugher, The neuroprotective effects of GLP-1:

Possible treatments for cognitive deficits in individuals with mood disorders. Behav. Brain Res. 2013 Jan. 15, 237:164-71.

i. Learning Disability

The compositions may be useful for treating or preventing learning disability. See, e.g., Roger S. McIntyre, Alissa M. Powell, Oksana Kaidanovich-Beilin, Joanna K. Soczynska, Mohammad Alsuwaidan, Hanna O. Woldeyohannes, Ashley S. Kim, L. Ashley Gallaugher, The neuroprotective effects of GLP-1: Possible treatments for cognitive deficits in individuals with mood disorders. Behav. Brain Res. 2013 Jan. 15, 237:164-71; and Mark P Mattson, TracyAnn Perry and Nigel H Greig, Learning from the gut. Nature Medicine 9, 1113-1115 (2003). An intestinal peptide that regulates glucose metabolism by stimulating insulin secretion from the pancreas is now shown to enhance learning and memory. The peptide can also protect nerve cells in models of neurodegenerative disorders (pages 1173-1179).

j. Asthma

The compositions may be useful for treating or preventing asthma.

k. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire®). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

l. Combination Therapies

Additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula (I). The above combinations include combinations of a compound of the present invention not only with one other active compound, but also with two or more other active compounds. For example, the compound of Formula (I) can be combined with a variety of DPPIV inhibitors, GLP-1 analogues, MC4 receptor agonists and positive allosteric modulators of MC4 such as, but not limited to, PF-00446687, PL-6983 and THIQ.

The compound of Formula (I) can be combined with the following DPPIV inhibitors, but not limited to: sitagliptin, vildagliptin, saxagliptin, linagliptin, anagliptin, teneligliptin, alogliptin, trelagliptin, omarigliptin, dutogliptin, gemigliptin.

The compound of Formula (I) can be combined with the following GLP-1 analogues, but not limited to: exenatide, liraglutide, lixisenatide, albiglutide, and dulaglutide.

The compound of Formula (I) can be combined with the following anxiolytics, but not limited to: buspirone, tandosprione, gepirone, adaptol, afobazole, hyroxyzine, validol, melatonin, and benzodiazepines such as alprazolam, chlordiazepoxide, clonazepam, diazepam, etizolam, lorazepam, oxazepam, and tofisopam.

The compound of Formula I can be combined with MC4 receptor agonists or positive allosteric modulators of MC4 (e.g., (3R,4R,5S)-1-([(3S,4R)-1-tert-butyl-4-(2,4-difluorophenyl) pyrrolidin-3-yl]carbonyl)-3,5-dimethyl-4-phenylpiperidin-4-ol ("PF-00446687"); PL-6983; and N-[(3R)-1,2, 3,4-tetrahydroisoquinolinium-3-ylcarbonyl]-(1R)-1-(4-chlorobenzyl)-2-[4-cyclohexyl-4-(1H-1,2,4-triazol-1ylmethyl)piperidin-1-yl]-2-oxoethylamine ("THIQ")).

The disclosed compounds may be included in kits comprising the compound [e.g., one or more compounds of formula (I)], a systemic or topical composition described above, or both; and information, instructions, or both that use of the kit will provide treatment for medical conditions in mammals (particularly humans). The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

The compounds and processes of the invention will be better understood by reference to the following examples, which are intended as an illustration of and not a limitation upon the scope of the invention.

5. Examples

All NMR spectra were recorded on a 400 MHz AMX Bruker NMR spectrometer. $^1$H chemical shifts are reported in δ values in ppm downfield with the deuterated solvent as the internal standard. Data are reported as follows: chemical shift, multiplicity (s=singlet, bs=broad singlet, d=doublet, t=triplet, q=quartet, dd=doublet of doublets, m=multiplet, ABq=AB quartet), coupling constant, integration. Reversed-phase LCMS analysis was performed using an Agilent 1200 system comprised of a binary pump with degasser, high-performance autosampler, thermostatted column compartment, C18 column, diode-array detector (DAD) and an Agilent 6150 MSD with the following parameters. The gradient conditions were 5% to 95% acetonitrile with the aqueous phase 0.1% TFA in water over 1.4 minutes. Samples were separated on a Waters Acquity UPLC BEH C18 column (1.7 μm, 1.0×50 mm) at 0.5 mL/min, with column and solvent temperatures maintained at 55° C. The DAD was set to scan from 190 to 300 nm, and the signals used were 220 nm and 254 nm (both with a band width of 4 nm). The MS detector was configured with an electrospray ionization source, and the low-resolution mass spectra were acquired by scanning from 140 to 700 AMU with a step size of 0.2 AMU at 0.13 cycles/second, and peak width of 0.008 minutes. The drying gas flow was set to 13 liters per minute at 300° C. and the nebulizer pressure was set to 30 psi. The capillary needle voltage was set at 3000 V, and the fragmentor voltage was set at 100V. Data acquisition was performed with Agilent Chemstation and Analytical Studio Reviewer software.

Example 1

(S)-2-Cyclopentyl-N-((1-isopropylpyrrolidin-2-yl)methyl)-10-methyl-1-oxo-1,2-dihydropyrazino[1,2-a]indole-4-carboxamide (Compound 1)

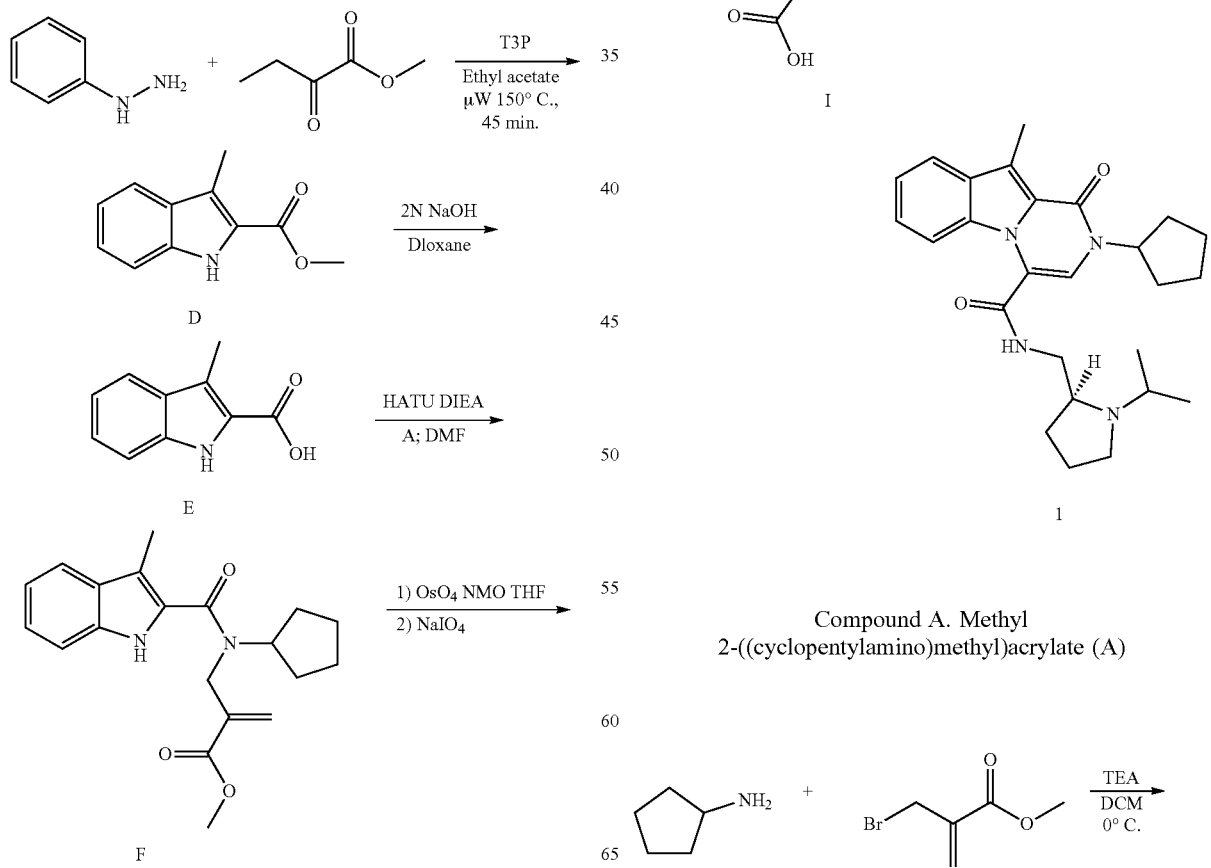

Compound A. Methyl 2-((cyclopentylamino)methyl)acrylate (A)

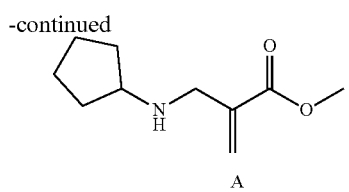

Methyl 2-((cyclopentylamino)methyl)acrylate (A)

Cyclopentylamine (5.79 mL, 58.7 mmol, 3.00 eq) and triethylamine (2.73 mL, 19.6 mL, 1.00 eq) were added to DCM (98 mL) and the reaction was cooled to 0° C. Methyl 2-(bromomethyl)acrylate (2.35 mL, 19.6 mmol, 1.00 eq) in DCM (48 mL) was added dropwise. Following addition the reaction was stirred for an additional 30 minutes at 0° C. Water was added and the layers separated. The aqueous layer was extracted with an additional portion of DCM and the combined organics were dried (MgSO$_4$), filtered and concentrated in vacuo. Purification by flash chromatography on silica gel using 0-60% DCM/MeOH/NH$_4$OH (89:10:1) afforded 1.19 g (33%) of the title compound as a clear oil: $^1$H NMR (400 MHz, DMSO-d$_6$) δ 6.10 (s, 1H), 5.79 (s, 1H), 3.67 (s, 3H), 3.65 (d, J=5.9 Hz, 1H), 3.56 (d, J=15.1 Hz, 1H), 3.21 (d, J=7.4 Hz, 1H), 2.98 (p, J=6.2 Hz, 1H), 1.72-1.22 (m, 8H); ES-MS [M+1]$^+$: 184.4.

Compound C.
(S)-(1-Isopropylpyrrolidin-2-yl)methanamine Dihydrochloride (C)

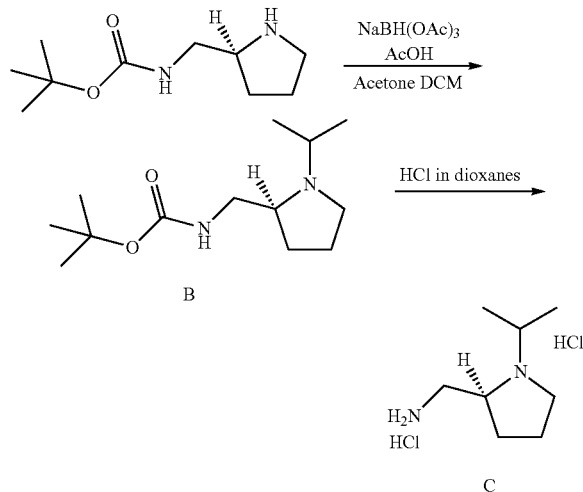

Tert-butyl (S)-((1-isopropylpyrrolidin-2-yl)methyl)carbamate (B)

(S)-2-N-Boc-aminomethylpyrrolidine (5.00 g, 25.0 mmol, 1.00 eq), acetone (3.10 mL, 49.9 mmol, 2.00 eq) and acetic acid (3.57 ml, 62.4 mmol, 2.50 eq) were dissolved in DCM (125 mL) and stirred at room temperature for three hours. Sodium triacetoxyborohydride (7.94 g, 37.4 mmol, 1.50 eq) was added and the reaction was allowed to stir overnight. The reaction was washed with saturated sodium bicarbonate and the layers separated. The aqueous layer was extracted with 3:1 CHCl$_3$/IPA (3:1) (2×) and the combined organics were dried (MgSO$_4$), filtered and concentrated in vacuo. Purification by flash chromatography on silica gel using 0-90% DCM/MeOH/NH$_4$OH (89:10:1) afforded 6.09 g (100%) of the title compound as a white solid: $^1$H NMR (400 MHz, DMSO-d$_6$) δ 6.69 (t, J=5.4 Hz, 1H), 2.97-2.91 (m, 1H), 2.77 (t, J=6.0 Hz, 2H), 2.74-2.67 (m, 1H), 2.61-2.54 (m, 1H), 2.42-2.33 (m, 1H), 1.63-1.50 (m, 4H), 1.36 (s, 9H), 1.03 (d, J=6.4 Hz, 3H), 0.92 (d, J=6.4 Hz, 3H); ES-MS [M+1]$^+$: 243.4.

(S)-(1-Isopropylpyrrolidin-2-yl)methanamine Dihydrochloride (C)

Compound 2 (6.09 g, 25.1 mmol, 1.00 eq) was suspended in 4N HCl in dioxane (63 mL). The reaction was stirred until determination of completion by LCMS. The reaction was concentrated to dryness to afford 5.40 g (99%) of the title compound as a brown solid that was used without further purification: $^1$H NMR (400 MHz, DMSO-d$_6$) δ 3.00-2.93 (m, 1H), 2.88-2.76 (m, 2H), 2.67-2.54 (m, 2H), 2.48-2.42 (m, 1H), 1.78-1.56 (m, 4H), 1.03 (d, J=6.5 Hz, 3H), 0.92 (d, J=6.3 Hz, 3H); ES-MS [M+1]$^+$: 143.2.

Methyl 3-methyl-1H-indole-2-carboxylate (D)

Phenylhydrazine (1.37 mL, 13.9 mmol, 1.00 eq), methyl 2-oxobutanoate (1.61 g, 13.9 mmol, 1.00 eq) and propylphosphonic anhydride solution (50 wt % in ethyl acetate) (17.7 mL, 27.7 mmol, 2.00 eq) were added to ethyl acetate (7 mL) in a microwave vial and heated in a microwave reactor at 180° C. for 30 minutes. The reaction was concentrated and the residue dissolved in ethyl acetate and washed with water. The organic layer was dried (MgSO$_4$), filtered and concentrated in vacuo. Purification by flash chromatography on silica gel using 0-20% hexanes/ethyl acetate afforded 2.26 g (86%) of the title compound as a white solid: $^1$H NMR (400 MHz, DMSO-d$_6$) δ 7.63 (d, J=8.1 Hz, 1H), 7.39 (d, J=8.3 Hz, 1H), 7.24 (t, J=7.2 Hz, 1H), 7.05 (t, J=7.4 Hz, 1H), 3.86 (s, 3H), 2.52 (s, 3H); ES-MS [M+1]$^+$: 190.3.

3-Methyl-1H-indole-2-carboxylic acid (E)

Compound D (2.26 g, 11.9 mmol, 1.00 eq) was dissolved in dioxane (60 mL) and 2N NaOH (23.9 mL, 23.9 mmol, 2.00 eq) was added. The reaction was stirred at room temperature until determination of completion by LCMS. The reaction was brought to pH 4-5 with 2N HCl and concentrated to dryness. The solid was suspended in 5% methanol/DCM and filtered to remove undissolved salt. The organics were concentrated to afford 2.09 g (100%) of the title compound as a brown solid that was used without further purification: $^1$H NMR (400 MHz, DMSO-d$_6$) δ 11.34 (s, 1H), 7.61 (d, J=8.0 Hz, 1H), 7.37 (d, J=8.3 Hz, 1H), 7.22 (t, J=7.2 Hz, 1H), 7.03 (t, J=7.5 Hz, 1H), 2.51 (s, 3H); ES-MS [M+1]$^+$: 176.4.

Methyl 2-(N-cyclopentyl-3-methyl-1H-indole-2-carboxamido)methyl)acrylate (F)

Compound E (700 mg, 4.00 mmol, 1.00 eq), compound A (1.47 g, 8.00 mmol, 2.00 eq), (1-[bis(dimethylamino)methylene]-1H-1,2,3-triazolo[4,5-b]pyridinium 3-oxid hexafluorophosphate) (1.82 g, 4.80 mmol, 1.20 eq) and N,N-diisopropylethylamine (1.39 mL, 8.00 mmol, 2.00 eq) were dissolved in DMF (20 mL) and stirred overnight. The reaction was diluted with ethyl acetate and washed with water (2×). The aqueous layer was back extracted with ethyl acetate and the combined organics were dried (MgSO$_4$), filtered and concentrated in vacuo. Purification by flash chromatography on silica gel using 0-40% hexanes/ethyl acetate afforded 914 mg (67%) of the title compound as a pale yellow solid: $^1$H NMR (400 MHz, DMSO-d$_6$) δ 11.22 (s, 1H), 7.52 (d, J=7.9 Hz, 1H), 7.33 (d, J=8.1 Hz, 1H), 7.14 (t, J=7.3 Hz, 1H), 7.02 (t, J=7.5 Hz, 1H), 6.21 (s, 1H), 5.75 (s, 1H), 4.31-4.20 (m, 1H), 4.19 (s, 2H), 3.71 (s, 3H), 2.25 (s, 3H), 1.79-1.68 (m, 2H), 1.65-1.49 (m, 4H), 1.44-1.32 (m, 2H); ES-MS [M+1]$^+$: 341.4.

Methyl 3-(N-cyclopentyl-3-methyl-1H-indole-2-carboxamido)-2-oxopropanoate (G)

Compound F (914 mg, 2.68 mmol, 1.00 eq) and N-methylmorpholine N-oxide (377 mg, 3.22 mmol, 1.20 eq) were dissolved in a mixture of THF (6.7 mL) and water (2.23 mL). Osmium tetroxide (2.5 wt. % in tert-butanol) (1.37 mL, 0.134 mmol, 0.0500 eq) was added and the reaction was stirred until complete disappearance of starting material was confirmed by LCMS. Sodium periodate (1.44 g, 6.71 mmol, 2.50 eq) was added and the reaction was stirred until determination of completion by LCMS. The reaction was diluted with ethyl acetate and washed with 10% sodium thiosulfate. The organic phase was dried (MgSO$_4$), filtered and concentrated in vacuo to afford 919 mg (100%) of the title compound as a brown solid that was used without further purification: $^1$H NMR (400 MHz, DMSO-d$_6$) δ 7.66-7.61 (m, 2H), 7.25 (t, J=7.5 Hz, 1H), 7.11 (t, J=7.7 Hz, 1H), 4.9 (p, 8.0 Hz, 1H), 3.85 (d, J=12.8 Hz, 1H), 3.72 (d, J=12.8 Hz, 1H), 3.64 (s, 3H), 2.56 (s, 3H), 1.78-1.62 (m, 4H), 1.60-1.44 (m, 4H); ES-MS [M+1]$^+$: 343.3.

Methyl 2-cyclopentyl-10-methyl-1-oxo-1,2-dihydropyrazino[1,2-a]indole-4-carboxylate (H)

Compound G (29 mg, 0.0847, 1.00 eq) was dissolved in THF (1 mL) and boron trifluoride diethyl etherate (0.0322 mL, 0.254 mmol, 3.00 eq) was added. The reaction was heated in a microwave reactor at 120° C. for 10 minutes and then diluted with ethyl acetate. The organics were washed with saturated sodium bicarbonate and the organic phase was dried (MgSO$_4$), filtered and concentrated in vacuo. Purification by flash chromatography on silica gel using 0-20% hexanes/ethyl acetate afforded 23 mg (84%) of the title compound as a yellow solid: $^1$H NMR (400 MHz, DMSO-d$_6$) δ 7.80 (d, J=7.9 Hz, 1H), 7.70 (d, J=8.7 Hz, 1H), 7.42 (s, 1H), 7.36 (t, J=7.4 Hz, 1H), 7.28 (t, J=7.7 Hz, 1H), 5.04 (p, 8.2 Hz, 1H), 3.92 (s, 3H), 2.73 (s, 3H), 2.05-1.94 (m, 2H), 1.86-1.60 (m, 6H); ES-MS [M+1]$^+$: 325.4.

2-Cyclopentyl-10-methyl-1-oxo-1,2-dihydropyrazino[1,2-a]indole-4-carboxylic acid (Compound I)

Compound H (171 mg, 0.527 mmol, 1.00 eq) was dissolved in dioxane (2.6 mL) and 2N NaOH (1.05 mL, 1.05 mmol, 2.00 eq) was added. The reaction was stirred at room temperature until determination of completion by LCMS. The reaction was brought to a pH 4-5 with 2N HCl and concentrated to dryness. The solid was suspended in 5% methanol/DCM and filtered to remove undissolved salt. The organics were concentrated to afford 165 mg (100%) of the title compound as a yellow solid that was used without further purification: $^1$H NMR (400 MHz, DMSO-d$_6$) δ 7.84 (d, J=8.6 Hz, 1H), 7.79 (d, J=8.0 Hz, 1H), 7.40 (s, 1H), 7.35 (t, J=7.3 Hz, 1H), 7.27 (t, J=7.6 Hz, 1H), 5.04 (p, J=8.0 Hz, 1H), 2.73 (s, 3H), 2.05-1.96 (m, 2H), 1.85-1.61 (m, 6H); ES-MS [M+1]$^+$: 311.2.

(S)-2-Cyclopentyl-N-((1-isopropylpyrrolidin-2-yl)methyl)-10-methyl-1-oxo-1,2-dihydropyrazino[1,2-a]indole-4-carboxamide (Compound 1)

Compound I (100 mg, 0.322 mmol, 1.00 eq), compound C (139 mg, 0.644 mmol, 2.00 eq), (1-[bis(dimethylamino)methylene]-1H-1,2,3-triazolo[4,5-b]pyridinium 3-oxid hexafluorophosphate) (147 mg, 0.387 mmol, 1.20 eq) and N,N-diisopropylethylamine (0.225 mL, 1.29 mmol, 4.00 eq) were dissolved in DMF (1.6 mL) and stirred overnight. The reaction was diluted with ethyl acetate and washed with water (2×). The aqueous layer was back extracted with ethyl acetate and the combined organics were dried (MgSO$_4$), filtered and concentrated in vacuo. Purification by reverse-phase chromatography afforded 121 mg (86%) of the title compound as a white solid: $^1$H NMR (400 MHz, DMSO-d$_6$) δ 8.84 (s, 1H), 7.79 (d, J=7.8 Hz, 1H), 7.64 (d, J=8.4 Hz, 1H), 7.34-7.23 (m, 2H), 6.81 (s, 1H), 5.12 (p, J=8.2 Hz, 1H), 3.3-2.8 (m, 6H), 2.74 (s, 3H), 2.03-1.94 (m, 2H), 1.86-1.61 (m, 10H), 1.07 (d, J=48.1 Hz, 6H); ES-MS [M+1]$^+$: 435.5.

The following compounds were prepared in an analogous manner with the appropriate starting materials:

| Compound No. | Name | Structure | ES-MS [M + 1]$^+$ |
|---|---|---|---|
| 2 | (R)-2-cyclopentyl-N-((1-isopropylpyrrolidin-2-yl)methyl)-10-methyl-1-oxo-1,2-dihydropyrazino[1,2-a]indole-4-carboxamide | 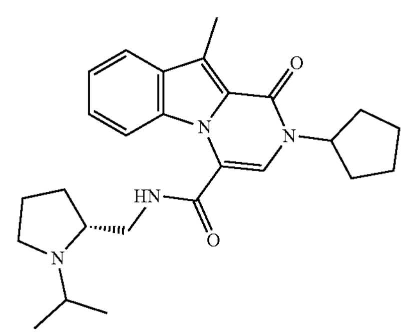 [SMILES: Cc1c2ccccc2n2c(C(=O)NC[C@H]3CCCN3C(C)C)cn(C3CCCC3)c(=O)c12] | |

-continued

| Compound No. | Name | Structure | ES-MS [M + 1]+ |
|---|---|---|---|
| 3 | 2-cyclopentyl-N-(((S)-1-isopropylpyrrolidin-2-yl)methyl)-10-methyl-1-oxo-1,2,3,4-tetrahydropyrazino[1,2-a]indole-4-carboxamide | 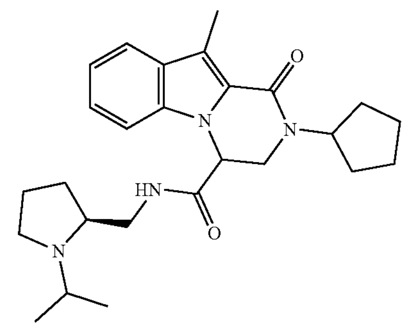 [SMILES: Cc1c2n(c3ccccc13)C(C(=O)NC[C@@H]1CCCN1C(C)C)CN(C1CCCC1)C2=O] | 437.4 |
| 4 | N-(((S)-1-isopropylpyrrolidin-2-yl)methyl)-10-methyl-1-oxo-2-((S)-tetrahydrofuran-3-yl)-1,2-dihydropyrazino[1,2-a]indole-4-carboxamide | 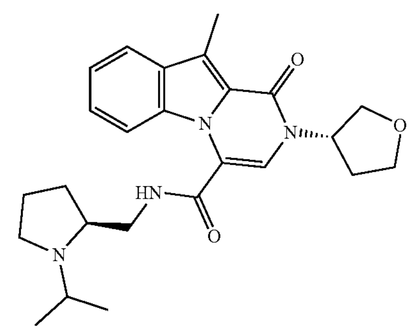 [SMILES: Cc1c2ccccc2n2c(C(=O)NC[C@@H]3CCCN3C(C)C)cn([C@H]3CCOC3)c(=O)c12] | 437.4 |
| 5 | N-(((R)-1-isopropylpyrrolidin-2-yl)methyl)-10-methyl-1-oxo-2-((S)-tetrahydrofuran-3-yl)-1,2-dihydropyrazino[1,2-a]indole-4-carboxamide | 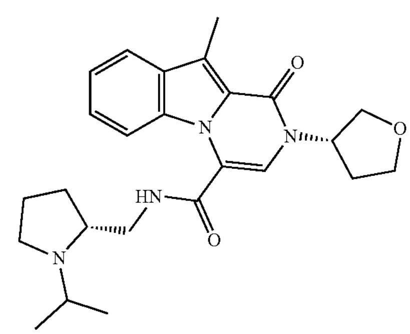 [SMILES: Cc1c2ccccc2n2c(C(=O)NC[C@H]3CCCN3C(C)C)cn([C@H]3CCOC3)c(=O)c12] | 437.4 |
| 6 | (S)-2-cyclopentyl-8-fluoro-N-((1-isopropylpyrrolidin-2-yl)methyl)-10-methyl-1-oxo-1,2-dihydropyrazino[1,2-a]indole-4-carboxamide | 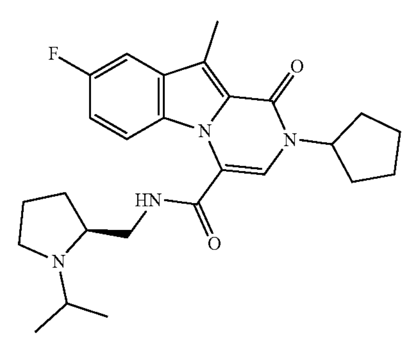 [SMILES: Cc1c2cc(F)ccc2n2c(C(=O)NC[C@@H]3CCCN3C(C)C)cn(C3CCCC3)c(=O)c12] | 453.4 |

-continued

| Compound No. | Name | Structure | ES-MS [M + 1]+ |
|---|---|---|---|
| 7 | (R)-2-cyclopentyl-8-fluoro-N-((1-isopropylpyrrolidin-2-yl)methyl)-10-methyl-1-oxo-1,2-dihydropyrazino[1,2-a]indole-4-carboxamide | 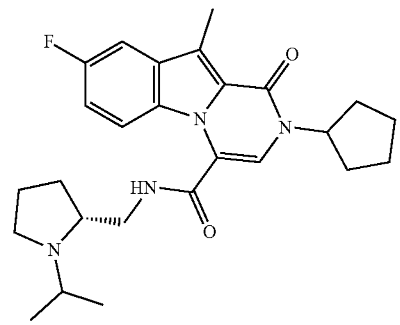 [SMILES: Cc1c2cc(F)ccc2n2c(C(=O)NC[C@H]3CCCN3C(C)C)cn(C3CCCC3)c(=O)c12] | 453.4 |
| 8 | (R)-2-cyclopentyl-N-(((S)-1-isopropylpyrrolidin-2-yl)methyl)-10-methyl-1-oxo-1,2,3,4-tetrahydropyrazino[1,2-a]indole-4-carboxamide | 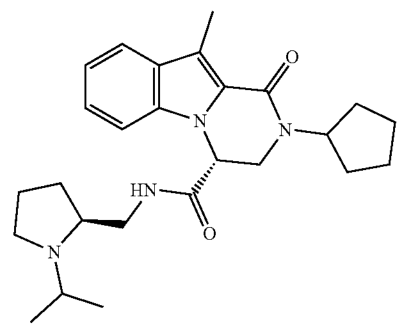 [SMILES: Cc1c2n(c3ccccc13)[C@@H](C(=O)NC[C@@H]1CCCN1C(C)C)CN(C1CCCC1)C2=O] | 437.5 |
| 9 | (S)-2-cyclopentyl-N-(((S)-1-isopropylpyrrolidin-2-yl)methyl)-10-methyl-1-oxo-1,2,3,4-tetrahydropyrazino[1,2-a]indole-4-carboxamide | 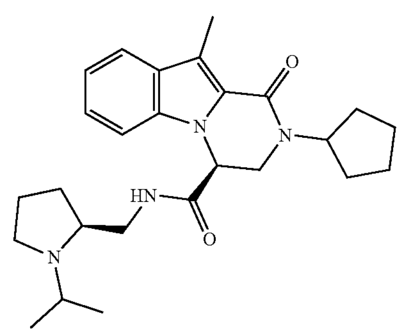 [SMILES: Cc1c2n(c3ccccc13)[C@H](C(=O)NC[C@@H]1CCCN1C(C)C)CN(C1CCCC1)C2=O] | 437.4 |
| 10 | (S)-10-chloro-2-cyclopentyl-N-((1-isopropylpyrrolidin-2-yl)methyl)-1-oxo-1,2-dihydropyrazino[1,2-a]indole-4-carboxamide | 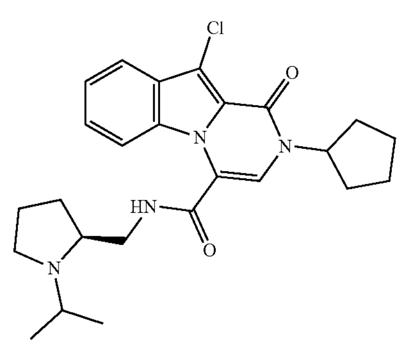 [SMILES: CC(C)N1CCC[C@H]1CNC(=O)c1cn(C2CCCC2)c(=O)c2c(Cl)c3ccccc3n12] | 455.4 |

| Compound No. | Name | Structure | ES-MS [M + 1]+ |
|---|---|---|---|
| 11 | (R)-10-chloro-2-cyclopentyl-N-((1-isopropylpyrrolidin-2-yl)methyl)-1-oxo-1,2-dihydropyrazino[1,2-a]indole-4-carboxamide | 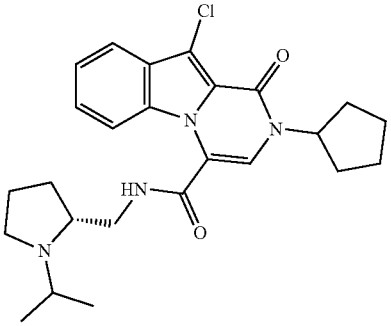 [SMILES: CC(C)N1CCC[C@@H]1CNC(=O)c1cn(C2CCCC2)c(=O)c2c(Cl)c3ccccc3n12] | 455.3 |
| 12 | (S)-10-bromo-2-cyclopentyl-N-((1-isopropylpyrrolidin-2-yl)methyl)-1-oxo-1,2-dihydropyrazino[1,2-a]indole-4-carboxamide | 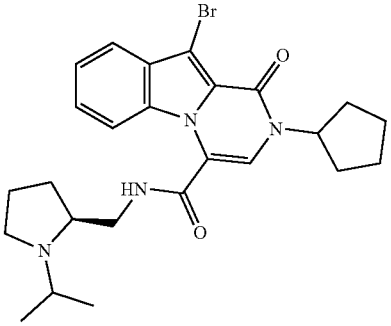 [SMILES: CC(C)N1CCC[C@H]1CNC(=O)c1cn(C2CCCC2)c(=O)c2c(Br)c3ccccc3n12] | 499.3 |
| 13 | (R)-10-bromo-2-cyclopentyl-N-((1-isopropylpyrrolidin-2-yl)methyl)-1-oxo-1,2-dihydropyrazino[1,2-a]indole-4-carboxamide | 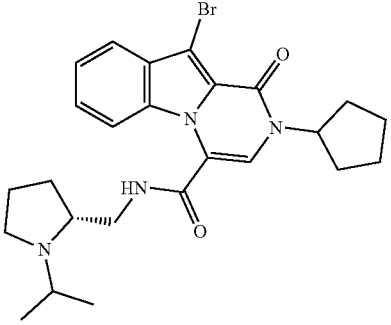 [SMILES: CC(C)N1CCC[C@@H]1CNC(=O)c1cn(C2CCCC2)c(=O)c2c(Br)c3ccccc3n12] | 499.3 |
| 14 | (S)-N-((1-isopropylpyrrolidin-2-yl)methyl)-10-methyl-1-oxo-2-phenyl-1,2-dihydropyrazino[1,2-a]indole-4-carboxamide | 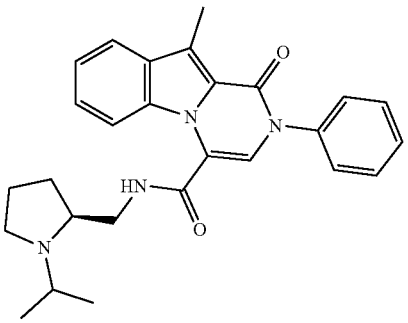 [SMILES: Cc1c2ccccc2n2c(C(=O)NC[C@@H]3CCCN3C(C)C)cn(-c3ccccc3)c(=O)c12] | 443.4 |

-continued

| Compound No. | Name | Structure | ES-MS [M + 1]+ |
|---|---|---|---|
| 15 | (R)-N-((1-isopropylpyrrolidin-2-yl)methyl)-10-methyl-1-oxo-2-phenyl-1,2-dihydropyrazino[1,2-a]indole-4-carboxamide | 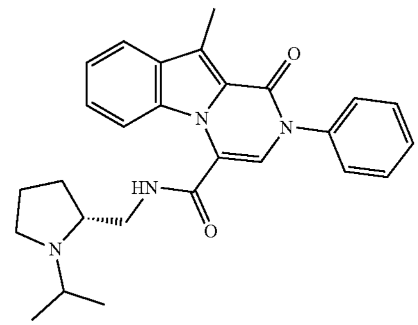 [SMILES: Cc1c2ccccc2n2c(C(=O)NC[C@H]3CCCN3C(C)C)cn(-c3ccccc3)c(=O)c12] | 443.4 |
| 16 | (S)-10-cyano-2-cyclopentyl-N-((1-isopropylpyrrolidin-2-yl)methyl)-1-oxo-1,2-dihydropyrazino[1,2-a]indole-4-carboxamide | 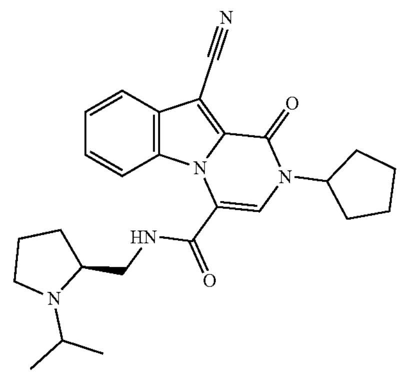 [SMILES: CC(C)N1CCC[C@H]1CNC(=O)c1cn(C2CCCC2)c(=O)c2c(C#N)c3ccccc3n12] | 446.4 |
| 17 | (S)-2-cyclopentyl-N-((1-isopropylpyrrolidin-2-yl)methyl)-1-oxo-10-vinyl-1,2-dihydropyrazino[1,2-a]indole-4-carboxamide | 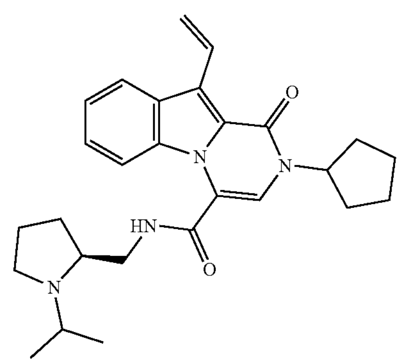 [SMILES: C=Cc1c2ccccc2n2c(C(=O)NC[C@@H]3CCCN3C(C)C)cn(C3CCCC3)c(=O)c12] | 447.4 |
| 18 | (S)-N-((1-isopropylpyrrolidin-2-yl)methyl)-10-methyl-2-(1-methyl-1H-pyrazol-4-yl)-1-oxo-1,2-dihydropyrazino[1,2-a]indole-4-carboxamide | 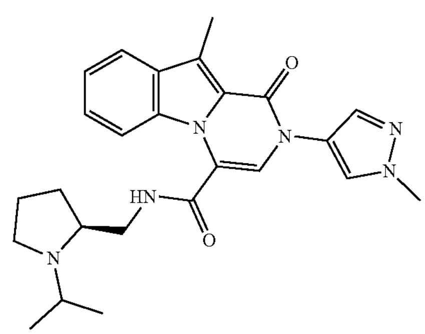 [SMILES: Cc1c2ccccc2n2c(C(=O)NC[C@@H]3CCCN3C(C)C)cn(-c3cnn(C)c3)c(=O)c12] | 447.4 |

-continued

| Compound No. | Name | Structure | ES-MS [M + 1]+ |
|---|---|---|---|
| 19 | (R)-N-((1-isopropylpyrrolidin-2-yl)methyl)-10-methyl-2-(1-methyl-1H-pyrazol-4-yl)-1-oxo-1,2-dihydropyrazino[1,2-a]indole-4-carboxamide | 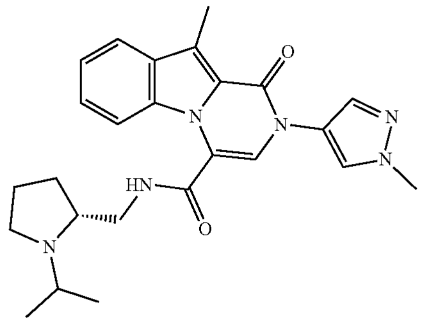 [SMILES: Cc1c2ccccc2n2c(C(=O)NC[C@H]3CCCN3C(C)C)cn(-c3cnn(C)c3)c(=O)c12] | 447.4 |
| 20 | (S)-N-((1-isopropylpyrrolidin-2-yl)methyl)-10-methyl-1-oxo-2-(pyridin-3-yl)-1,2-dihydropyrazino[1,2-a]indole-4-carboxamide | 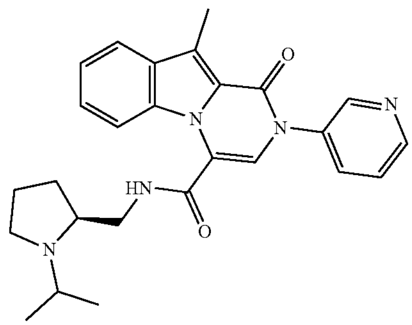 [SMILES: Cc1c2ccccc2n2c(C(=O)NC[C@@H]3CCCN3C(C)C)cn(-c3cccnc3)c(=O)c12] | 444.4 |
| 21 | (R)-N-((1-isopropylpyrrolidin-2-yl)methyl)-10-methyl-1-oxo-2-(pyridin-3-yl)-1,2-dihydropyrazino[1,2-a]indole-4-carboxamide | 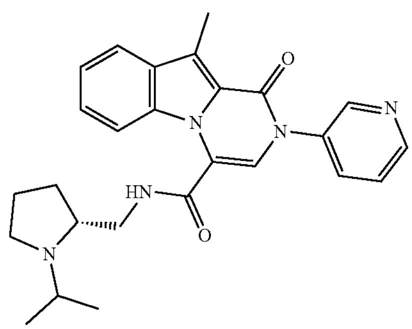 [SMILES: Cc1c2ccccc2n2c(C(=O)NC[C@H]3CCCN3C(C)C)cn(-c3cccnc3)c(=O)c12] | 444.4 |
| 22 | N-(azetidin-2-ylmethyl)-2-cyclopentyl-10-methyl-1-oxo-1,2-dihydropyrazino[1,2-a]indole-4-carboxamide | 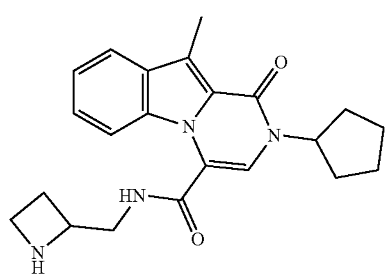 [SMILES: Cc1c2ccccc2n2c(C(=O)NCC3CCN3)cn(C3CCCC3)c(=O)c12] | 379.4 |
| 23 | 2-cyclopentyl-4-(hydroxymethyl)-10-methylpyrazino[1,2-a]indol-1(2H)-one | 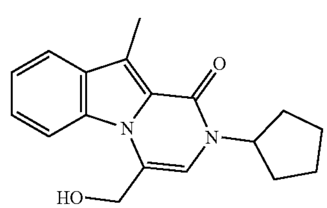 [SMILES: Cc1c2ccccc2n2c(CO)cn(C3CCCC3)c(=O)c12] | 297.4 |

| Compound No. | Name | Structure | ES-MS [M + 1]+ |
|---|---|---|---|
| 24 | 2-cyclopentyl-N-((1-isopropylazetidin-2-yl)methyl)-10-methyl-1-oxo-1,2-dihydropyrazino[1,2-a]indole-4-carboxamide | 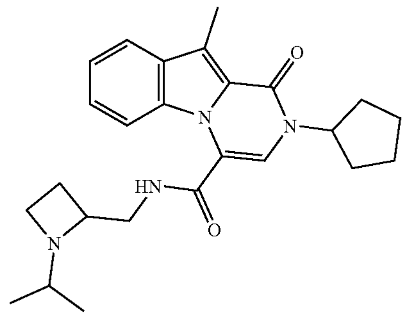 [SMILES: Cc1c2ccccc2n2c(C(=O)NCC3CCN3C(C)C)cn(C3CCCC3)c(=O)c12] | 421.4 |

Biological Activity

A. GLP-1 Assay with GLP1 Endogenous Agonist

To assess the effects of test compounds on GLP-1 or glucagon potency and efficacy, a high-throughput calcium mobilization assay was used essentially as previously described (Morris L C, Days E L, Turney M, Mi D, Lindsley C W, Weaver C D, Niswender K D, A Duplexed High-Throughput Screen to Identify Allosteric Modulators of the Glucagon-Like Peptide 1 and Glucagon Receptors. J. Biomol. Screen. 2014 Feb. 13, 19(6):847-858). Briefly, human GLP-1R or Glucagon Receptor 9-3-H cells overexpressing a promiscuous G-protein (Millipore, Billerica, Mass.) were plated at 15,000 cells/well in black-walled 384-well plates (Greiner Bio-one, Monroe, N.C.) in Dulbecco's Modified Eagles Medium (DMEM) with 10% FCS, 4.0 mM L-glutamine, non-essential amino acids (NEAAs), and 10.0 mM HEPES without antibiotics. After overnight attachment, cells were washed twice with assay buffer (HBSS supplemented with 20 mM HEPES and 1.0 mM probenecid) using an ELx405CW cell washer (Bio-Tek, Winooski, Vt.) and then loaded with the calcium sensitive dye fluo-4 AM (Invitrogen, Grand Island, N.Y.) at a final concentration of 2.0 µM in assay buffer. After a 45-minute incubation at room temperature, the dye was removed by washing, leaving 20 µL of assay buffer. Next, the cell plate was introduced alongside a 384-well compound plate containing 0.1% final DMSO control wells and 11-point concentration response curves of putative GLP-1 PAMs created using a non-pipet based liquid transfer instrument, ECH0555 (Labcyte, Sunnyvale, Calif.). After a 20 µL compound addition to the appropriate wells, kinetic fluorescent measurements were collected for 2 minutes using an FDSS6000 (Hamamatsu, Bridgewater, N.J.) with 488 nm excitation and 480/540 emission filters. After 2 minutes, 10 µL of an $EC_{20}$ concentration of GLP-1 peptide 7-36 amide (Phoenix Pharmaceuticals, Burlingame, Calif.), Glucagon (Phoenix Pharmaceuticals, Burlingame, Calif.) Exendin-4 (Tocris Bioscience, Bristol, UK), or Liraglutide (Victoza™, Novo-Nordisk, Denmark) was added and fluorescence was monitored for an additional 2 minutes to observe potentiation of the calcium flux signal. Control wells for vehicle, $EC_{20}$ peptide, and $E_{max}$ peptide resided in columns #1 and 24 and rows H and I to account for any plate variations. Recombinant peptides were reconstituted into assay buffer supplemented with 0.1% fatty acid free BSA (Sigma #A6003) and diluted into borosilicate glass tubes to maximize peptide recovery (Goebel-Stengel M, Stengel A, Tache Y, Reeve J R Jr., The importance of using the optimal plasticware and glassware in studies involving peptides. Anal. Biochem. 2011 Jul. 1, 414(1):38-46).

B. GLP-1 Assay with EX-4 Synthetic Agonist

To assess the effects of test compounds on GLP-1 or glucagon potency and efficacy, a high-throughput calcium mobilization assay was used essentially as previously described (Morris L C, Days E L, Turney M, Mi D, Lindsley C W, Weaver C D, Niswender K D, A Duplexed High-Throughput Screen to Identify Allosteric Modulators of the Glucagon-Like Peptide 1 and Glucagon Receptors. J. Biomol. Screen. 2014 Feb. 13, 19(6):847-858). Briefly, human GLP-1R or Glucagon Receptor 9-3-H cells overexpressing a promiscuous G-protein (Millipore, Billerica, Mass.) were plated at 15,000 cells/well in black-walled 384-well plates (Greiner Bio-one, Monroe, N.C.) in Dulbecco's Modified Eagles Medium (DMEM) with 10% FCS, 4.0 mM L-glutamine, 1× non-essential amino acids (NEAAs), and 10.0 mM HEPES without antibiotics. After overnight attachment, cells were washed twice with assay buffer (HBSS supplemented with 20 mM HEPES and 1.0 mM probenecid) using an ELx405CW cell washer (Bio-Tek, Winooski, Vt.) and then loaded with the calcium sensitive dye fluo-4 AM (Invitrogen, Grand Island, N.Y.) at a final concentration of 2.0 µM in assay buffer. After a 45-minute incubation at room temperature, the dye was removed by washing, leaving 20 µL of assay buffer. Next, the cell plate was introduced alongside a 384-well compound plate containing 0.1% final DMSO control wells and 11-point concentration response curves of putative GLP-1 PAMs created using a non-pipet based liquid transfer instrument, ECH0555 (Labcyte, Sunnyvale, Calif.). After a 20 µL compound addition to the appropriate wells, kinetic fluorescent measurements were collected for 2 minutes using an FDSS6000 (Hamamatsu, Bridgewater, N.J.) with 488 nm excitation and 480/540 emission filters. After 2 minutes, 10 µL of an $EC_{20}$ concentration of EX-4 (Phoenix Pharmaceuticals, Burlingame, Calif.), Glucagon (Phoenix Pharmaceuticals, Burlingame, Calif.) Exendin-4 (Tocris Bioscience, Bristol, UK), or Liraglutide (Victoza™, Novo-Nordisk, Denmark) was added and fluorescence was monitored for an additional 2 minutes to observe potentiation of the calcium flux signal. Control wells for vehicle, $EC_{20}$ peptide, and $E_{max}$ peptide resided in columns #1 and 24 and rows H and I to account for any plate variations. Recombinant peptides were reconstituted into assay buffer supplemented with 0.1% fatty acid free BSA (Sigma #A6003) and diluted into borosilicate glass tubes to maximize peptide recovery (Goebel-Stengel M, Stengel A, Taché Y, Reeve J R Jr., The importance of using the optimal plasticware and glassware in studies involving peptides. Anal. Biochem. 2011 Jul. 1, 414(1):38-46).

B. Results and Discussion of Biological Activity Data

The results of these assays are shown in Table 1. The data in Table 1 demonstrates that the disclosed compounds are positive allosteric modulators of GLP-1 receptor. Data is from a single experiment unless otherwise noted. Data that is an average of two experiments is noted as "n=2" while data that is an average of three or more experiments is presented as the average plus or minus the standard error of the mean.

TABLE 1

| Compound No. | % $E_{max}$ (endogenous GLP1) (30 μM) | GLP1 $EC_{50}$ (endogenous GLP1) (μM) | % $E_{max}$ (Ex-4 synthetic agonist) (30 μM) | GLP1 $EC_{50}$ (Ex-4 synthetic agonist) (μM) |
|---|---|---|---|---|
| I | — | >30 | — | — |
| 1 | 57% | 2.7 | 59% | 4.6 |
| 2 | — | >30 | — | >30 |
| 3 | 50% | 5.7 | 55% | 11 |
| 4 | 52% | 2.4 | 50% | 2.9 |
| 5 | 56% | 4.2 | 55% | 5.9 |
| 6 | 60% | 4.4 | 54% | 6.1 |
| 7 | — | >30 | — | >30 |
| 8 | 56% | 3.6 | 56% | 3.6 |
| 9 | 40% | >30 | 33% | >30 |
| 10 | 61% | 1.3 | 57% | 1.5 |
| 11 | 44% | >30 | — | >30 |
| 12 | 53% | 2.2 | 59% | 3.6 |
| 13 | 39% | >30 | — | >30 |
| 14 | 45% | 13 | | |
| 15 | — | >30 | | |
| 16 | 43% | 1.9 | | |
| 17 | 37% | 9.6 | | |
| 18 | 34% | 6.7 | | |
| 19 | — | >30 | | |
| 20 | 36% | 5.2 | | |
| 21 | — | >30 | | |
| 22 | — | >30 | | |
| 23 | — | >30 | | |
| 24 | 51% | 12 | | |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:
1. A compound of formula (I-c),

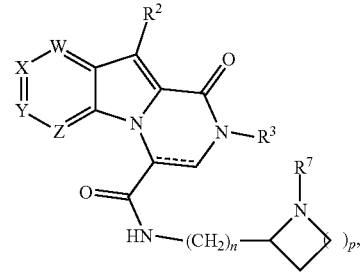

(I-c)

or a pharmaceutically acceptable salt thereof; wherein
p is 1 or 2;
W, X, Y and Z are each $CR^1$;
$R^1$ is hydrogen;
$R^2$ is $C_1$-$C_3$ alkyl, $C_2$-$C_4$ alkenyl, cyano, or halogen;
$R^3$ is $C_3$-$C_6$ cycloalkyl, phenyl, pyridyl, pyrazolyl, or tetrahydrofuranyl, wherein $R^3$ is substituted with 0-3 substituents independently selected from $C_1$-$C_3$ alkyl;
n is 1 and
$R^7$ is hydrogen or $C_1$-$C_3$ alkyl.

2. The compound of claim 1, or a pharmaceutically acceptable salt thereof, wherein $R^7$ is isopropyl.

3. The compound of claim 1, wherein the compound is selected from the group consisting of:
(S)-2-cyclopentyl-N-((1-isopropylpyrrolidin-2-yl)methyl)-10-methyl-1-oxo-1,2-dihydropyrazino[1,2-a]indole-4-carboxamide;
(R)-2-cyclopentyl-N-((1-isopropylpyrrolidin-2-yl)methyl)-10-methyl-1-oxo-1,2-dihydropyrazino[1,2-a]indole-4-carboxamide;
2-cyclopentyl-N-q(S)-1-isopropylpyrrolidin-2-yl)methyl)-10-methyl-1-oxo-1,2,3,4-tetrahydropyrazino[1,2-a]indole-4-carboxamide;
N—(((S)-1-isopropylpyrrolidin-2-yl)methyl)-10-methyl-1-oxo-2-((S)-tetrahydrofuran-3-yl)-1,2-dihydropyrazino[1,2-a]indole-4-carboxamide;
N—(((R)-1-isopropylpyrrolidin-2-yl)methyl)-10-methyl-1-oxo-2-((S)-tetrahydrofuran-3-yl)-1,2-dihydropyrazino[1,2-a]indole-4-carboxamide;
(S)-2-cyclopentyl-8-fluoro-N-((1-isopropylpyrrolidin-2-yl)methyl)-10-methyl-1-oxo-1,2-dihydropyrazino[1,2-a]indole-4-carboxamide;
(R)-2-cyclopentyl-8-fluoro-N-((1-isopropylpyrrolidin-2-yl)methyl)-10-methyl-1-oxo-1,2-dihydropyrazino[1,2-a]indole-4-carboxamide;
(R)-2-cyclopentyl-N—(((S)-1-isopropylpyrrolidin-2-yl)methyl)-10-methyl-1-oxo-1,2,3,4-tetrahydropyrazino[1,2-a]indole-4-carboxamide;
(S)-2-cyclopentyl-N—(((S)-1-isopropylpyrrolidin-2-yl)methyl)-10-methyl-1-oxo-1,2,3,4-tetrahydropyrazino[1,2-a]indole-4-carboxamide;
(S)-10-chloro-2-cyclopentyl-N-((1-isopropylpyrrolidin-2-yl)methyl)-1-oxo-1,2-dihydropyrazino[1,2-a]indole-4-carboxamide;
(R)-10-chloro-2-cyclopentyl-N-((1-isopropylpyrrolidin-2-yl)methyl)-1-oxo-1,2-dihydropyrazino[1,2-a]indole-4-carboxamide;
(S)-10-bromo-2-cyclopentyl-N-((1-isopropylpyrrolidin-2-yl)methyl)-1-oxo-1,2-dihydropyrazino[1,2-a]indole-4-carboxamide;
(R)-10-bromo-2-cyclopentyl-N-((1-isopropylpyrrolidin-2-yl)methyl)-1-oxo-1,2-dihydropyrazino[1,2-a]indole-4-carboxamide;

(S)—N-((1-isopropylpyrrolidin-2-yl)methyl)-10-methyl-1-oxo-2-phenyl-1,2-dihydropyrazino[1,2-a]indole-4-carboxamide;
(R)—N-((1-isopropylpyrrolidin-2-yl)methyl)-10-methyl-1-oxo-2-phenyl-1,2-dihydropyrazino[1,2-a]indole-4-carboxamide;
(S)-10-cyano-2-cyclopentyl-N-((1-isopropylpyrrolidin-2-yl)methyl)-1-oxo-1,2-dihydropyrazino[1,2-a]indole-4-carboxamide;
(S)-2-cyclopentyl-N-((1-isopropylpyrrolidin-2-yl)methyl)-1-oxo-10-vinyl-1,2-dihydropyrazino[1,2-a]indole-4-carboxamide;
(S)—N-((1-isopropylpyrrolidin-2-yl)methyl)-10-methyl-2-(1-methyl-1H-pyrazol-4-yl)-1-oxo-1,2-dihydropyrazino[1,2-a]indole-4-carboxamide;
(R)—N-((1-isopropylpyrrolidin-2-yl)methyl)-10-methyl-2-(1-methyl-1H-pyrazol-4-yl)-1-oxo-1,2-dihydropyrazino[1,2-a]indole-4-carboxamide;
(S)—N-((1-isopropylpyrrolidin-2-yl)methyl)-10-methyl-1-oxo-2-(pyridin-3-yl)-1,2-dihydropyrazino[1,2-a]indole-4-carboxamide;
(R)—N-((1-isopropylpyrrolidin-2-yl)methyl)-10-methyl-1-oxo-2-(pyridin-3-yl)-1,2-dihydropyrazino[1,2-a]indole-4-carboxamide;
N-(azetidin-2-ylmethyl)-2-cyclopentyl-10-methyl-1-oxo-1,2-dihydropyrazino[1,2-a]indole-4-carboxamide; and
2-cyclopentyl-N-((1-isopropylazetidin-2-yl)methyl)-10-methyl-1-oxo-1,2-dihydropyrazino[1,2-a]indole-4-carboxamide;
or a pharmaceutically acceptable salt thereof.

4. A pharmaceutical composition comprising the compound of claim 1, or a pharmaceutically acceptable salt thereof, and a pharmaceutically acceptable carrier.

5. The compound of claim 1, or a pharmaceutically acceptable salt thereof, of formula (I-d)

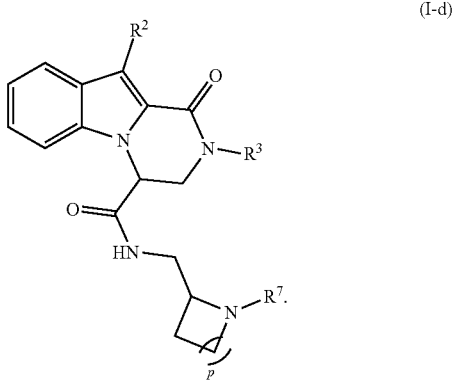

(I-d)

6. The compound of claim 1, or a pharmaceutically acceptable salt thereof, of formula (I-d')

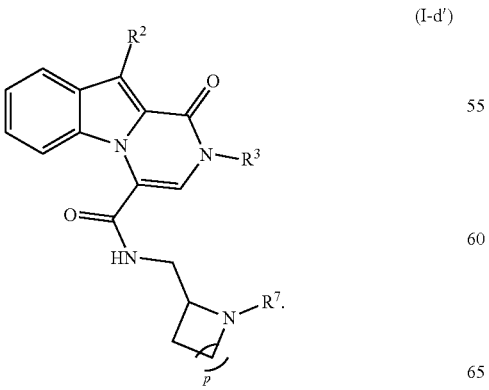

(I-d')

7. The compound of claim 1, or a pharmaceutically acceptable salt thereof, of formula (I-e)

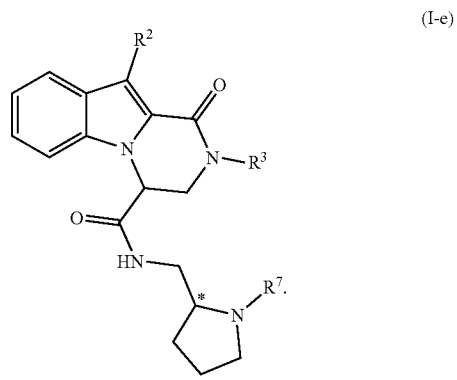

(I-e)

8. The compound of claim 1, or a pharmaceutically acceptable salt thereof, of formula (I-e')

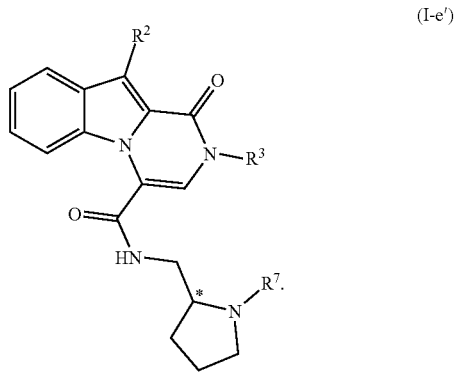

(I-e')

9. The compound of claim 1, or a pharmaceutically acceptable salt thereof, of formula (I-f)

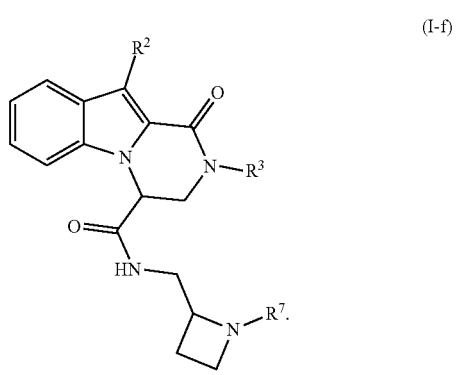

(I-f)

10. The compound of claim 1, or a pharmaceutically acceptable salt thereof, of formula (I-f)

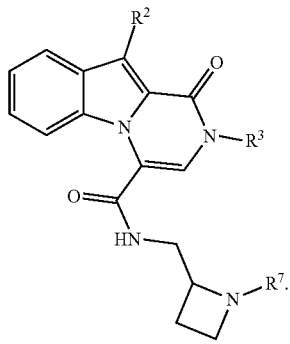

(I-f')

11. The compound of claim 1, or a pharmaceutically acceptable salt thereof, wherein $R^2$ is methyl, vinyl, fluoro, chloro, bromo, or cyano.

12. The compound of claim 5, or a pharmaceutically acceptable salt thereof, wherein $R^2$ is methyl, vinyl, fluoro, chloro, bromo, or cyano.

13. The compound of claim 6, or a pharmaceutically acceptable salt thereof, wherein $R^2$ is methyl, vinyl, fluoro, chloro, bromo, or cyano.

14. The compound of claim 7 or a pharmaceutically acceptable salt thereof, wherein $R^2$ is methyl, vinyl, fluoro, chloro, bromo, or cyano.

15. The compound of claim 8, or a pharmaceutically acceptable salt thereof, wherein $R^2$ is methyl, vinyl, fluoro, chloro, bromo, or cyano.

16. The compound of claim 9, or a pharmaceutically acceptable salt thereof, wherein $R^2$ is methyl, vinyl, fluoro, chloro, bromo, or cyano.

17. The compound of claim 10, or a pharmaceutically acceptable salt thereof, wherein $R^2$ is methyl, vinyl, fluoro, chloro, bromo, or cyano.

* * * * *